(12) United States Patent
Pratt et al.

(10) Patent No.: US 8,436,999 B2
(45) Date of Patent: May 7, 2013

(54) FLUORESCENCE EXCITATION AND DETECTION SYSTEM AND METHOD

(75) Inventors: Mark Pratt, Belmont, CA (US); Jason Bryant, Cambridge (GB)

(73) Assignee: Illumina, Inc., San Diego, CA (US)

( * ) Notice: Subject to any disclaimer, the term of this patent is extended or adjusted under 35 U.S.C. 154(b) by 486 days.

(21) Appl. No.: 12/679,652

(22) PCT Filed: Sep. 26, 2008

(86) PCT No.: PCT/US2008/077850
§ 371 (c)(1),
(2), (4) Date: Mar. 23, 2010

(87) PCT Pub. No.: WO2009/042862
PCT Pub. Date: Apr. 2, 2009

(65) Prior Publication Data
US 2010/0193704 A1   Aug. 5, 2010

Related U.S. Application Data

(60) Provisional application No. 60/975,939, filed on Sep. 28, 2007.

(51) Int. Cl.
*G01N 21/00* (2006.01)
(52) U.S. Cl.
USPC .......................................... 356/432; 356/435
(58) Field of Classification Search .......... 356/432–436, 356/311, 317–320; 250/208.1, 208.2, 458.1, 250/459.1, 586; 600/476–477, 310, 317
See application file for complete search history.

(56) References Cited

U.S. PATENT DOCUMENTS

| | | | |
|---|---|---|---|
| 7,329,860 B2 | 2/2008 | Feng et al. | |
| 7,768,638 B2 | 8/2010 | Feng | |
| 2004/0245350 A1 | 12/2004 | Zeng | |

FOREIGN PATENT DOCUMENTS

| | | |
|---|---|---|
| EP | 0121262 | 10/1984 |
| WO | 03060589 | 7/2003 |
| WO | 2007123744 | 11/2007 |
| WO | 2007135368 | 11/2007 |

OTHER PUBLICATIONS

Lehr, H.P. et al; "Real-Time Detection of Nucleic Acid Interactions by Total Internal Reflection Fluorescence"; Analytical Chemistry, vol. 75, No. 10, May 15, 2003, 2414-2420.
Erdogan, Dr. Turan; "New Optical Filters Improve High-Speed Multicolor Fluorescence Imaging"; Mar. 2006; Biophotonics International (c) Lauren Publishing Co. Inc.; 6 pgs.
International Search Report and Written Opinion; PCT/US2008/077850; 13 pgs.

*Primary Examiner* — Tri T Ton
(74) *Attorney, Agent, or Firm* — The Small Patent Law Group LLC; Dean Small; Jason P. Gross

(57) ABSTRACT

A detection system for separately detecting different wavelengths of emission light emitted from a sample. The system includes a detection assembly to receive the emission light emitted from the sample. The detection assembly includes a multi-band dichroic member and at least first and second detection cameras. The multi-band dichroic member has a transmission/reflection characteristic with at least two transmissive regions separated from each other along a wavelength spectrum and with at least one reflective region separated from the transmissive regions along the wavelength spectrum. The dichroic member transmits portions of the emission light that align with the at least two transmissive regions to the first detection camera. The dichroic member reflects a portion of the emission light that aligns with the reflective region to the second detection camera.

26 Claims, 13 Drawing Sheets

US 8,436,999 B2

FLUORESCENCE EXCITATION AND DETECTION SYSTEM AND METHOD

CROSS-REFERENCE TO RELATED APPLICATIONS

The present application is a national stage of International Application No. PCT/US2008/077850, filed Sep. 26, 2008, which claims priority to and the benefit of U.S. Provisional Patent Application No. 60/975,939, filed Sep. 28, 2007, both of which are hereby incorporated by reference in their entirety.

BACKGROUND OF THE INVENTION

Embodiments of the present invention relate to the field of nucleic acid sequencing, and more specifically, embodiments of the present invention provide methods, systems and devices that utilize a plurality of excitation wavelengths to image multiple emission patterns through an optical detection path comprised of stationary components.

Numerous recent advances in the study of biology have benefited from improved methods for analyzing and sequencing of nucleic acids. For example, the Human Genome Project has determined the entire sequence of the human genome which is hoped to lead to further discoveries in fields ranging from treatment of disease to advances in basic science. Devices for DNA sequencing based on separation of fragments of differing length were first developed in the 1980s, and have been commercially available for a number of years. However, such technology involves running individual samples through capillary columns filled with polyacrylamide gels and is thus limited in throughput due to the time taken to run each sample. A number of new DNA sequencing technologies have recently been reported that are based on the massively parallel analysis of unamplified, or amplified single molecules, either in the form of planar arrays or on beads.

The methodology used to analyze the sequence of the nucleic acids in such new sequencing techniques is often based on the detection of fluorescent nucleotides or oligonucleotides. The detection instrumentation used to read the fluorescence signals on such arrays is usually based on either epifluorescence or total internal reflection microscopy. One detection instrument has been proposed that use an optical sequencing-by-synthesis (SBS) reader. The SBS reader includes a laser that induces fluorescence from a sample within water channels of a flowcell. The fluorescence is emitted and collected by imaging optics which comprise one or more objective lens and tube lens. As the fluorescence travels along an optics path within the imaging optics, but prior to reaching a detection camera, the fluorescence propagates through an interference emission filter. The emission filter has the ability to select wavelength bands of interest from the fluorescence and block other wavelength bands that are associated with noise, such as laser scatter or the emission from orthogonal fluorophores that emit at different wavelengths.

One conventional approach to performing spectral splitting of fluorescence is to use bandpass filters in conjunction with an emission filter wheel, where an emission filter wheel is located along the optical path before each detection camera. The emission filter wheel is a mechanical device that is rotated, under control of a servo motor, until an appropriate filter is placed in the optical path of the fluorescence. However, the use of filter wheels and servo motors in the detection path is not always desirable. As an example of the use of a mechanical filter wheel in operation, a high throughput sequencing instrument that is capable of capturing an image every few hundred milliseconds, means that in the course of a single days use, the filter wheel is used hundreds of thousands of times. During operation, the filter wheel is mechanically rotated between imaging cycles which introduces complexity and a filter switching time that reduces the overall operation rate of the detection system. Also, because the filter wheel is a mechanically moving element, it and other moving elements will have a limited life span and may introduce error over time as the elements wear. Finally, care is needed to properly align and calibrate the filter wheel.

There is a continuing need for better, more robust, and more economical devices and systems for fast reliable sequencing of nucleic acids. Embodiments of the present invention seek to address these needs and offer other benefits which will be apparent upon examination of the current specification, claims, and figures.

SUMMARY OF THE INVENTION

In accordance with an embodiment of the present invention, a detection system is provided for separately detecting different wavelengths of emission light emitted from a sample. The system comprises a detection assembly to receive emission light emitted from the sample. The detection assembly includes a multi-band dichroic member and at least first and second detection cameras. The multi-band dichroic member has a transmission/reflection characteristic with at least two transmissive regions separated from each other along the wavelength spectrum and with at least one reflective region separated from the transmissive regions along the wavelength spectrum. The dichroic member transmits emission light that aligns with the at least two transmissive regions to the first detection camera. The dichroic member reflects emission light that aligns with the reflective region to the second detection camera. The dichroic member multiplexes the detection of emission light signals without the use of a filter wheel in the detection assembly. The components of the detection assembly remain stationary throughout imaging of multiple colors, for example therefore allowing the use of two detectors to record images of three or more colors without the need for filter wheels or other moving components.

In accordance with at least one embodiment, the system comprises an excitation assembly to excite the sample. Optionally, the dichroic member comprises a single dichroic mirror having an incident surface with a transmissive/reflective spectrum comprising first and second transmissive regions, where the first transmissive region passes fluorescence emitted in response to a first excitation wavelength, while the second transmissive region passes fluorescence emitted in response to a second excitation wavelength. In accordance with at least one embodiment, the excitation assembly sequentially generates first and second excitation beams of different wavelengths during an illumination/detection cycle of an analysis process. The first and second excitation beams are generated repeatedly during consecutive excitation events of the analysis process. Each excitation event may comprise illumination with a single wavelength, or with multiple wavelengths. Optionally, the detection assembly may comprise a dual band dichroic member, at least two detection cameras and at least two band pass filters aligned between the dual band dichroic member and a corresponding one of the detection cameras. Optionally, the detection cameras may comprise first and second detection cameras aligned with the dichroic member such that fluorescence transmitted to the dichroic member impinges on the first detection camera and fluorescence reflected by the dichroic member impinges on the second detection camera, both in response to a single excitation event.

In accordance with an alternative embodiment, a method is provided for separately detecting fluorescence emitted at different wavelengths from a sample. The method comprises exciting a sample with at least first and second excitation wavelengths. The sample has first, second and third labels. Each label emits fluorescence at a different wavelength. The first and second labels are excited by the first excitation wavelength and the third label is excited by the second excitation wavelength. The method further comprises directing the fluorescence emitted from the sample onto a detection assembly. The detection assembly includes a multi-band dichroic member configured to have a transmission/reflection characteristic with at least two transmissive regions separated from each other along the wavelength spectrum and with at least one reflective region separated from the transmissive regions along the wavelength spectrum. The method further comprises transmitting fluorescence, that aligns with the transmissive regions, through the dichroic member along a transmissive detection path to a first detection camera. The method further comprises reflecting fluorescence, that aligns with the reflective region, from the dichroic member along a reflective detection path to a second detection camera and detecting fluorescence at the first and second detection cameras, such that the first and second labels are detected simultaneously on different ones of the first and second detection cameras, and the first and third labels are detected on a common one of the first and second detection cameras.

Optionally, the excitation operation may sequentially generate first and second excitation beams of different wavelengths during a cycle of an analysis process, where the first and second excitation beams each generate fluorescence with at least two spectral patterns of interest that are directed by the dichroic member along the transmissive and reflective detection paths. The dichroic member constitutes a non-moving part that remains stationary and fixed with respect to the sample and with respect to the transmissive and reflective detection paths throughout the analysis process.

In accordance with an alternative embodiment, an excitation and detection system is provided for separately detecting different wavelengths of emission light emitted from a sample. The system comprises an excitation assembly to excite a sample sequentially with first and second wavelengths during first and second excitation events in an illumination/detection cycle, respectively. The sample emits emission light with first and second spectral patterns in response to the first and second excitation wavelengths, respectively. A detection camera receives and measures at least a portion of the emission light with the first spectral pattern during a first measurement phase of the illumination/detection cycle. The detection camera receives and measures at least a portion of the emission light with the second spectral pattern during a second measurement phase of the illumination/detection cycle. The detection camera outputs first and second data signals representative of measured portions of the first and second spectral patterns.

Optionally, the emission light may represent various types of luminescent light, such as fluorescence, bioluminescence, electroluminescence, radioluminescence and any other emission light produced by a sample, where the emission light generates a plurality of known spectral patterns that are separable or distinguishable from one another along the wavelength spectrum. Optionally, the excitation source may be omitted entirely, such as when the sample utilizes chemiluminescence or radioluminescence and the like.

Optionally, the labels used in one or more of the systems and methods described herein may comprise a plurality of labeled nucleotides including at least four labeling dyes that emit unique fluorescence spectral patterns corresponding to the four nucleotides G, T, A and C. In response to a first excitation wavelength, the dichroic member may reflect a first spectral pattern and transmit a second spectral pattern. In response to the second excitation wavelength, the dichroic member may reflect a third spectral pattern and transmit a fourth spectral pattern, thus allowing the detection of four colors using two illumination events and two detection cameras, with no moving parts in the detection assembly.

DETAILED DESCRIPTION

Embodiments of the present invention comprise excitation and detection systems and methods for detecting fluorescence emitted from a sample. The sample has a plurality of labels, where each label emits fluorescence having a corresponding spectral pattern along a wavelength spectrum (emission spectrum). For example, the systems and methods may be used to analyze a large number of different nucleic acid sequences from, e.g., clonally amplified single-molecule DNA arrays in flowcells, or from an array of immobilized beads. The systems herein are optionally useful in, e.g., sequencing for comparative genomics (such as for genotyping, SNP discovery, BAC-end sequencing, chromosome breakpoint mapping, and whole genome sequence assembly), tracking gene expression, micro RNA sequence analysis, epigenomics (e.g., with methylation mapping DNAseI hypersensitive site mapping or chromatin immunoprecipitation), and aptamer and phage display library characterization. Of course, those of skill in the art will readily appreciate that the current invention is also amenable to use for myriad other sequencing applications. The systems herein comprise various combinations of optical, mechanical, fluidic, thermal, electrical, and computing devices/aspects which are described more fully below. Also, even though certain embodiments are directed towards particular configurations and/or combinations of such aspects, those of skill in the art will appreciate that not all embodiments necessarily comprise all aspects or particular configurations (unless specifically stated to do so).

As used throughout, the term "wavelength" shall not be limited to a single wavelength unless expressly stated to constitute "a single wavelength" or "only one wavelength". Instead, the term "wavelength" shall encompass a narrow range of wavelengths located about a desired or target wavelength (e.g., 532 nm±10 nm, 660 nm±15 nm).

The exemplary embodiments described herein are discussed in connection with the use of fluorescence as a type of emission light produced by a sample. However, the present invention is not limited to systems and methods that utilize fluorescence. Instead, the emission light may represent various types of luminescent light, other than fluorescence, such as bioluminescence, electroluminescence, radioluminescence and any other emission light produced by a sample, where the emission light generates a plurality of known spectral patterns that are separable or distinguishable from one another along the wavelength spectrum. In certain embodiments, the excitation source may be omitted entirely, such as when the sample utilizes chemiluminescence or radioluminescence and the like.

System Overview

Figure 1:
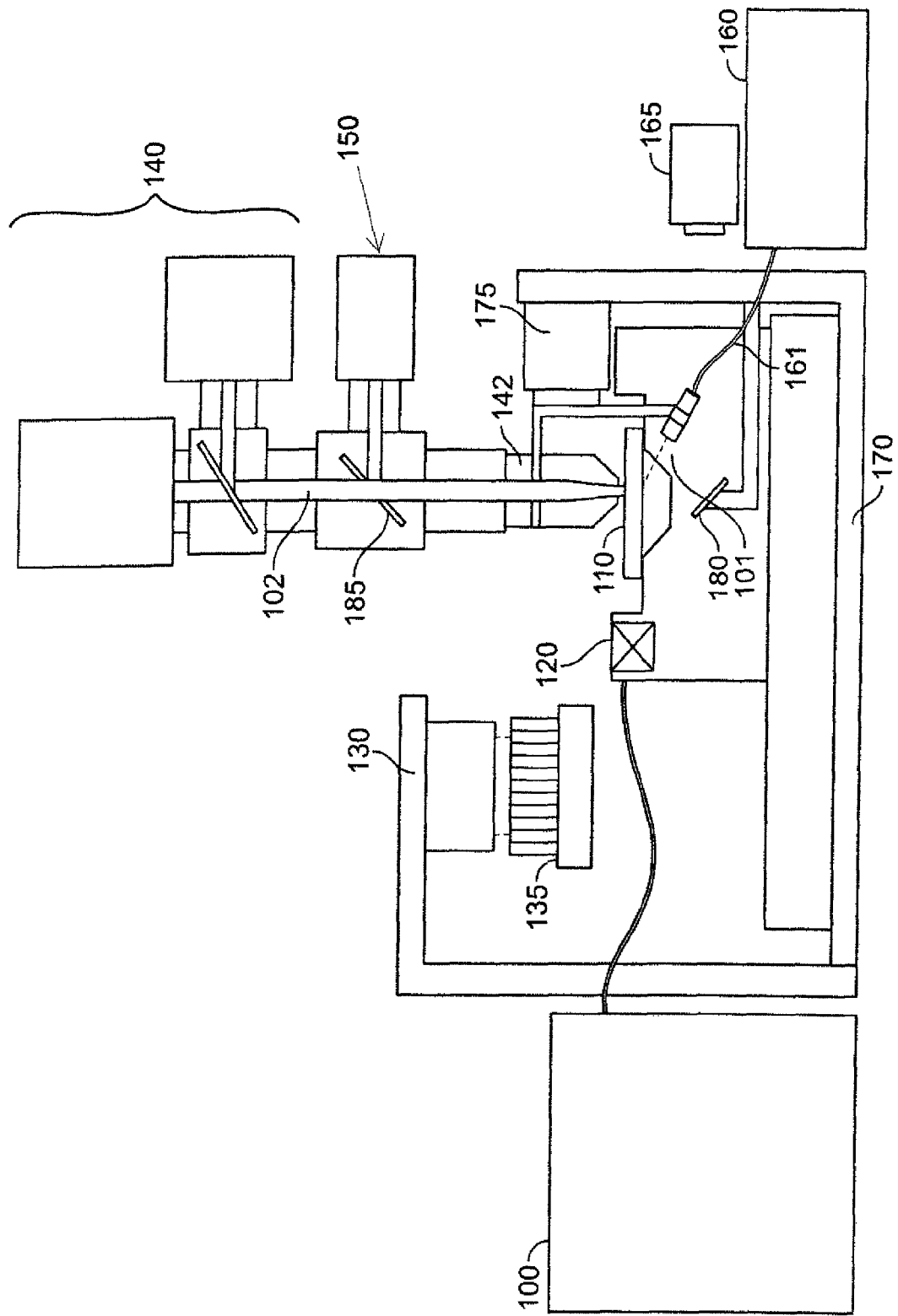
FIG. 1 illustrates a generalized overview of the components of a sequencing system formed in accordance with an embodiment of the present invention.

FIG. 1 shows an exemplary imaging configuration that utilizes total internal reflection fluorescence. By way of example, the system of FIG. 1 may be constructed to include various components and assemblies as described in international application publication no. WO 2007/123744, titled "System and Devices for Sequence by Synthesis Analysis", filed Mar. 30, 2007, the complete subject matter of which is incorporated herein by reference in its entirety. As can be seen in FIG. 1, fluid delivery module or device 100 directs the flow of reagents (e.g., fluorescent nucleotides, buffers, enzymes, cleavage reagents, etc.) to (and through) flowcell 110 and waste valve 120. The flow cell 110 may represent a substrate having one or more samples provided on or in the substrate. in particular embodiments, the flowcell 110 comprises clusters of nucleic acid sequences (e.g., of about 200-1000 bases in length) to be sequenced which are optionally attached to the substrate of the flowcell 110, as well as optionally to other components. The flowcell 110 may also comprise an array of beads, where each bead optionally contains multiple copies of a single sequence.

The system also comprises temperature station actuator 130 and heater/cooler 135, which can optionally regulate the temperature of conditions of the fluids within the flowcell 110. The flowcell 110 is monitored, and sequencing is tracked, by detection assembly 140 which can interact with focusing assembly 150. Excitation assembly 160 (e.g., one or more excitation lasers within an assembly) acts to illuminate fluorescent sequencing reactions within the flowcell 110 via laser illumination through fiber optic 161 (which can optionally comprise one or more re-imaging lenses, a fiber optic mounting, etc.). Low watt lamp 165 (optional), mirror 180 and reverse dichroic 185 are also presented in the embodiment shown. Additionally, mounting stage 170, allows for proper alignment and movement of the flowcell 110, temperature actuator 130, detection assembly 140, etc. in relation to the various components of the system. Focus (z-axis) component 175 can also aid in manipulation and positioning of various components (e.g., a lens objective). Such components are optionally organized upon a framework and/or enclosed within a housing structure. It will be appreciated that the illustrations herein are of exemplary embodiments and are not necessarily to be taken as limiting. Thus, for example, different embodiments can comprise different placement of components relative to one another (e.g., embodiment A comprises a heater/cooler as in FIG. 1, while embodiment B comprises a heater/cooler component beneath its flowcell, etc.).

Certain embodiments utilizes sequencing-by-synthesis (SBS). In SBS, a plurality of fluorescently labeled modified nucleotides are used to sequence dense clusters of amplified DNA (possibly millions of clusters) present on the surface of a substrate (e.g., a flowcell).

In particular uses of the systems/devices herein the flowcells 110, containing the nucleic acid samples for sequencing, are placed within the appropriate flowcell holder. The samples for sequencing can take the form of single molecules, amplified single molecules in the form of clusters, or beads comprising molecules of nucleic acid. The nucleic acids are prepared such that they comprise an oligonucleotide primer adjacent to an unknown target sequence. To initiate the first SBS sequencing cycle, one or more differently labeled nucleotides, and DNA polymerase, etc., are flowed into/through the flowcell by the fluid flow subsystem (various embodiments of which are described herein). Either a single nucleotide can be added at a time, or the nucleotides used in the sequencing procedure can be specially designed to possess a reversible termination property, thus allowing each cycle of the sequencing reaction to occur simultaneously in the presence of all four labeled nucleotides (A, C, T, G). Where the four nucleotides are mixed together, the polymerase is able to select the correct base to incorporate and each sequence is extended by a single base.

The heating/cooling components of the system regulate the reaction conditions within the flowcell channels and reagent storage areas/containers (and optionally the camera, optics, and/or other components), while the fluid flow components allow the substrate surface to be exposed to suitable reagents for incorporation (e.g., the appropriate fluorescently labeled nucleotides to be incorporated) while unincorporated reagents are rinsed away. During laser excitation by the excitation assembly 160, the image/location of emitted fluorescence from the nucleic acids on the substrate is captured by the detection assembly 140, thereby, recording the identity, in the computer component, of the first base for each single molecule, cluster or bead.

The various embodiments of the present invention present several novel features (again, it will be appreciated that not all features are present in all embodiments). For example, the systems herein can use two or more excitation lasers coupled through one or more fiberoptic devices to illuminate a common area (i.e. the illuminated areas, or footprints, of the lasers at least partially overlap). Additionally, embodiments may contain a shaking, squeezed, or waveplate modulated fiber (mode scrambler) such that the optical intensity from a multimode beam is made uniform over the whole illumination footprint. The shape of the fiber 161 may be adjusted, for example to be square or rectangular, such that the shape of the illumination can be matched to the shape of the data collection device (e.g., a CCD with square pixels). Also, in certain embodiments, a single laser excites two fluorophores, which are detected using different emission filters, one with a narrow band emission filter near the laser wavelength, and one with a wider band emission filter at a wavelength longer than the laser wavelength. Such arrangement may 'normalize' the relative intensities of the two dyes (with the same bandwidth filters, the dye further from the laser wavelength may be weaker due to its lower level of off-wavelength excitation). The embodiments herein also can comprise a moving stage such that the chemistry (which utilizes cycles of heating and cooling) can happen on the same instrument, but out of the optical train. The systems herein may also contain an autofocus system to allow automated imaging of many tiles, and contain a fluidics system for performing on-line fluidic changes. The individual components of the system/device (e.g., light source, camera, etc.) can optionally each have its own power source or supply or can optionally all be powered via one source. As will be appreciated, while the components herein are often described in isolation or in relation to only one or two other components, the various components in the embodiments are typically operably and/or functionally connected and work together in the systems/devices herein.

Flowcells

In various embodiments, the systems and methods herein comprise one or more substrates upon which the nucleic acids to be sequenced are bound, attached or associated. In certain embodiments, the substrate is within a channel or other area as part of a "flowcell." The flowcells used in the various embodiments can comprise millions of individual nucleic acid clusters, e.g., about 2-8 million clusters per channel. Each of such clusters can give read lengths of at least 25 bases for DNA sequencing and 20 bases for gene expression analysis. The systems and methods herein can generate over a gigabase (one billion bases) of sequence per run (e.g., 5 million nucleic acid clusters per channel, 8 channels per flowcell, 25 bases per polynucleotide).

Figure 4A:
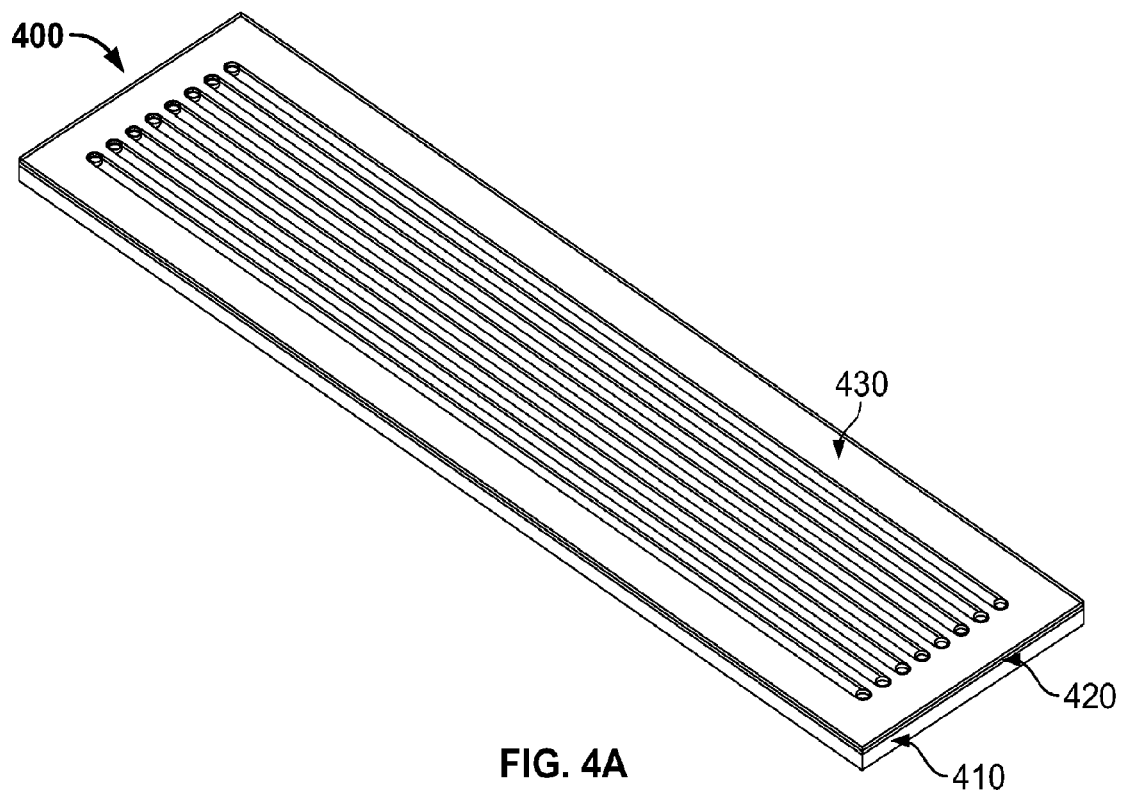
FIGS. 4A-4D show exemplary configurations of flowcells used in the sequencing system of FIG. 1.
Figure 4B:
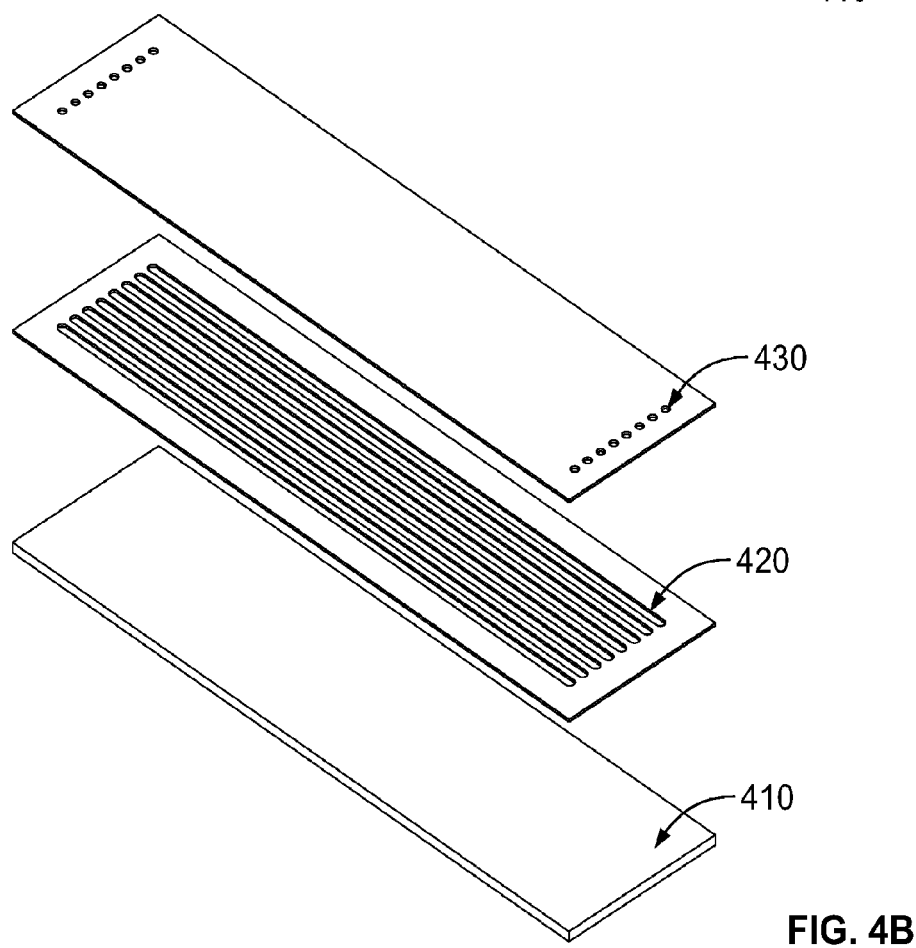

FIGS. 4A and 4B display one exemplary embodiment of a flowcell. As can be seen, the particular flowcell embodiment, flowcell 400, comprises base layer 410 (e.g., of borosilicate glass 1000 μm in depth), channel layer 420 (e.g., of etched silicon 100 μm in depth) overlaid upon the base layer, and cover, or top, layer 430 (e.g., 300 μm in depth). When the layers are assembled together, enclosed channels are formed having inlets/outlets at either end through the cover. As will be apparent from the description of additional embodiments below, some flowcells can comprise openings for the channels on the bottom of the flowcell.

Figure 4C:
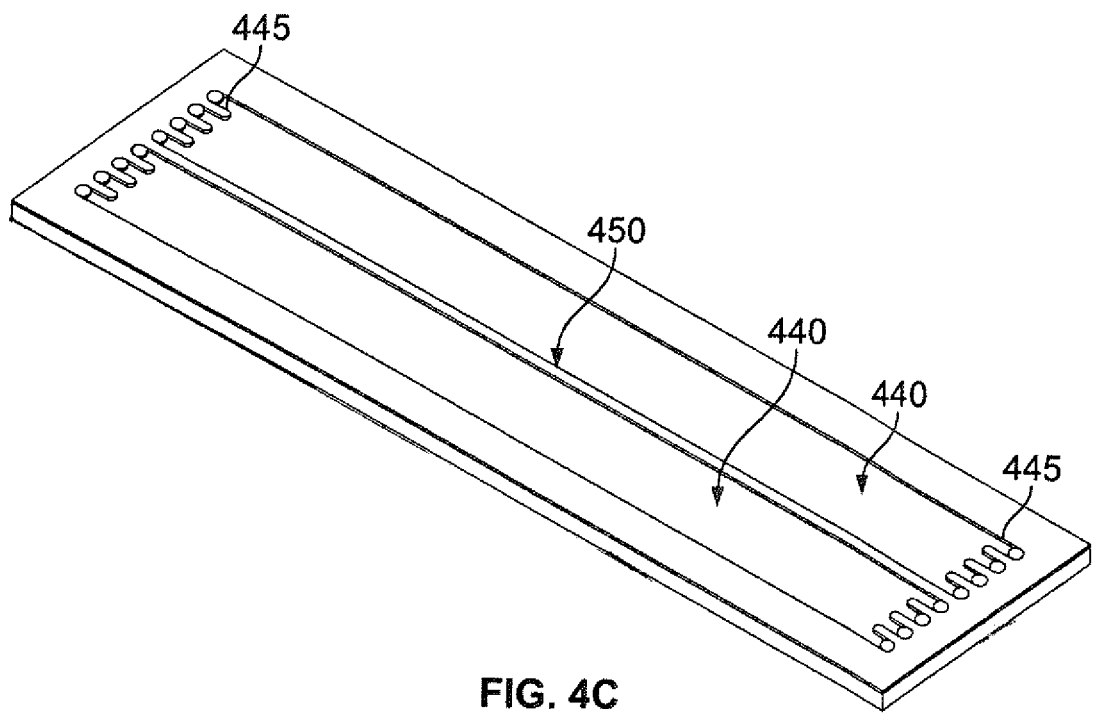
Figure 4D:
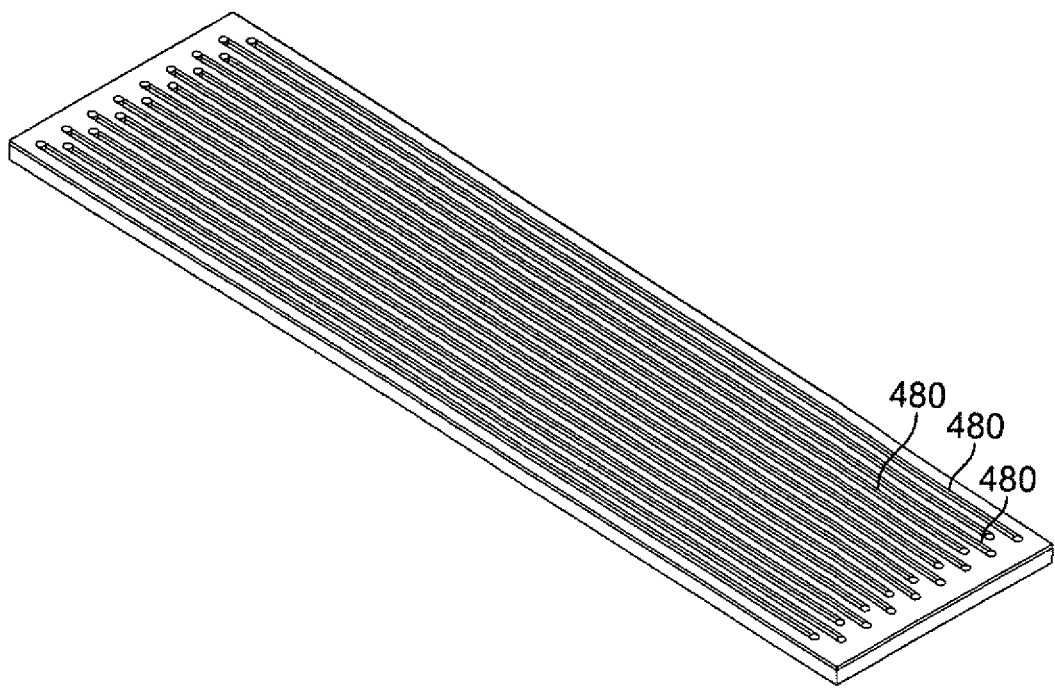

It will be appreciated that while particular flowcell configurations are present herein, such configurations should not necessarily be taken as limiting. Thus, for example, various flowcells herein can comprise different numbers of channels (e.g., 1 channel, 2 or more channels, 4 or more channels, or 6, 8, 10, 16 or more channels, etc.). Additionally, various flowcells can comprise channels of different depths and/or widths (different both between channels in different flowcells and different between channels within the same flowcell). For example, while the channels formed in the cell in FIG. 4B are 100 μm deep, other embodiments can optionally comprise channels of greater depth (e.g., 500 μm) or lesser depth (e.g., 50 μm). Additional exemplary flowcell designs are shown in FIGS. 4C and 4D (for example, a flowcell with "wide" channels, such as channels 440 in FIG. 4C, may have two channels with 8 inlet and outlet ports (ports 445—8 inlet and 8 outlet) to maintain flow uniformity and a center wall, such as wall 450, for added structural support. As another example, the flow cell may have offset channels, such as the 16 offset channels (channels 480).

Excitation and Detection Assembly

In certain embodiments herein, the incorporation of specific nucleic acid bases with their accompanying specific fluorescences is tracked via source excitation and camera observation. In various embodiments, illumination is performed using Total Internal Reflection (TIR) comprising a laser component. It will be appreciated that a "TIRF laser," "TIRF laser system," "TIR laser," and other similar terminology herein refers to a TIRF (Total Internal Reflection Fluorescence) based detection instrument/system using excitation, e.g., lasers or other types of non-laser excitation from such light sources as LED, halogen, and xenon or mercury arc lamps (all of which are also included in the current description of TIRF, TIRF laser, TIRF laser system, etc. herein). Thus, a "TIRF laser" is a laser used with a TIRF system, while a "TIRF laser system" is a TIRF system using a laser, etc. Again, however, the systems herein (even when described in terms of having laser usage, etc.) should also be understood to include those systems/instruments comprising non-laser based excitation sources. In some embodiments, the laser comprises dual individually modulated 50 mW to 500 mW solid state and/or semiconductor lasers coupled to a TIRF prism, optionally with excitation wavelengths of 532 nm and 660 nm. The coupling of the laser into the instrument can be via an optical fiber to help ensure that the footprints of the two lasers are focused on the same or common area of the substrate (i.e., overlap).

In certain embodiments, the systems and methods herein comprise component(s) to produce a "top-hat" illumination, e.g., a uniform or substantially uniform illumination over a particular illumination footprint. Some embodiments comprise one or more aspects that dynamically change the index of refraction within the medium transmitting the illumination (e.g., a fiber) at one or more nodes. For example, a fiber can be squeezed at various locations along its length to induce a continuously changing index of refraction. Such squeezing of the fiber, e.g., a Step Index Fiber, can be used to spatially/temporally scramble the modes in the fiber to cause sufficient overlap over a desired integration time of the output illumination. The fiber can also be shaken, rotated, vibrated or physically deformed in other ways to change the optical path through the fiber.

In general, the dynamic scrambling of the modes in the fibers allows achievement of spatially uniform illumination over a minimum user defined integration time. This thus prevents interference of propagating modes of monochromatic light in multimode fibers which would produce light and dark patterns in the resulting beam. It is optionally sufficient that these modes disappear over the minimum integration time. Thus, in some embodiments, the relative path lengths of these modes within the illumination beam are rapidly varied by introducing time variable curvature and index variations into the fiber, e.g., by mechanical means.

It will be appreciated that several parameters of the dynamic mode scrambling can optionally be varied or can comprise a range of different configurations. However, in general, dynamic mode scrambling comprises one or more aspects/components used to dynamically change the index of refraction of an illumination beam in order to average out an end illumination footprint.

Figure 2:
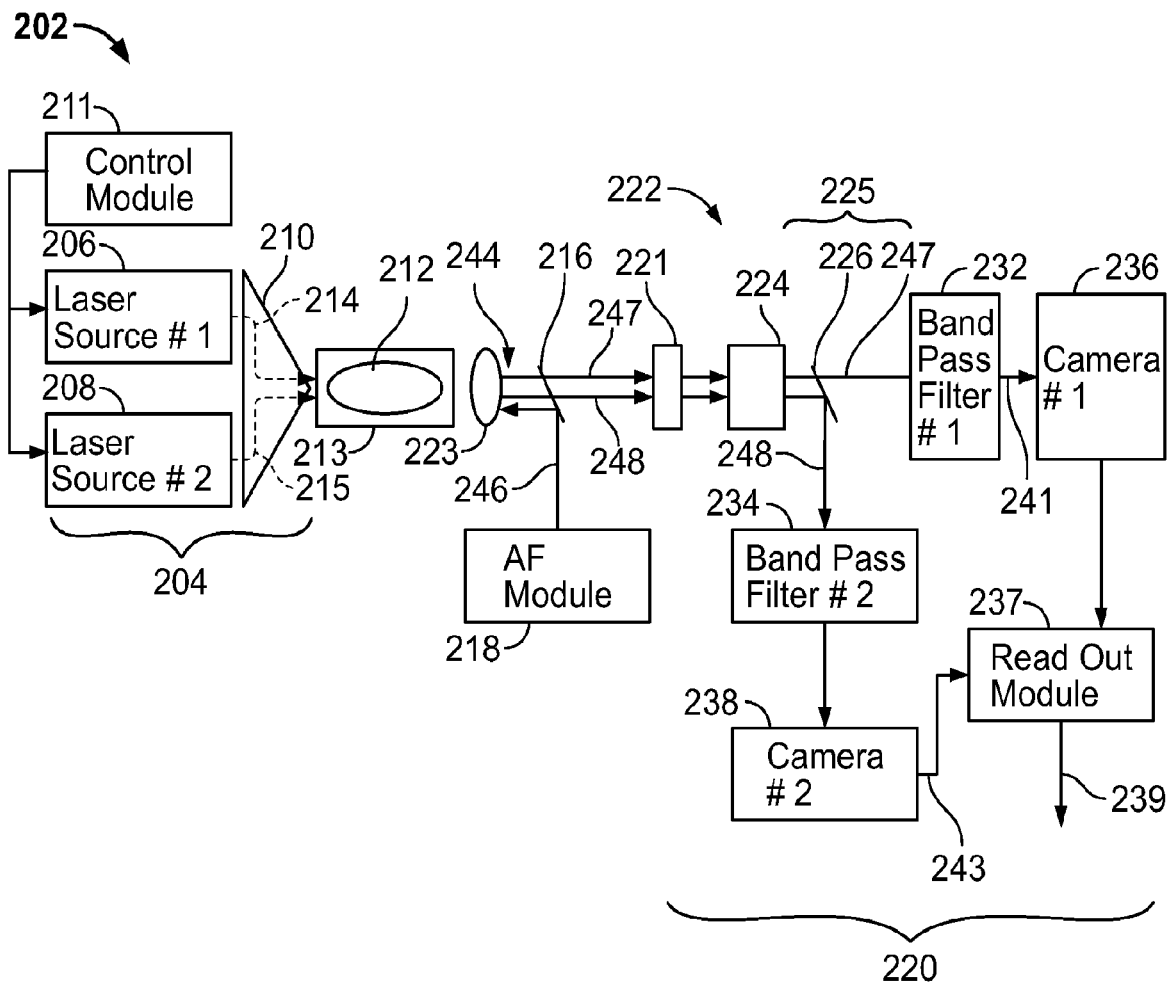
FIG. 2 illustrates a block diagram of an excitation and detection system formed in accordance with an embodiment of the present invention.

FIG. 2 illustrates an excitation and detection system 202 that is formed in accordance with an embodiment of the present invention. The excitation and detection system 202 generally includes an excitation assembly 204, an autofocus (AF) module 218 and a detection assembly 220. The excitation assembly 204 (corresponding to excitation assembly 160 in FIG. 1) is optically coupled to a sample 212 that is, in turn, optically coupled to the AF module 218 and the detection assembly 220 (corresponding to the detection assembly 140 in FIG. 1). The sample 212 is provided on a substrate 213, such as described in connection with FIGS. 1 and 4A-4C. For example, the sample 212 may represent a plurality of nucleic acid clusters/beads, with multiple fluorescent labels, which are attached to a surface of the substrate 213 (e.g., a flow cell). The excitation and detection assemblies 204 and 220 can provide a full field of view examination of the entire sample 212. For example, the excitation assembly 204 illuminates the entire surface or active area of each tile of the substrate within the flow cell 110 each time an excitation or illumination event occurs. Illumination of multiple consecutive tiles allows for large areas of the substrate to be imaged. The excitation assembly 204 illuminates the same or common active area, or tile, in a temporally multiplexed manner with one or more different excitation wavelengths during successive excitation events. The excitation assembly 204 performs temporal multiplexing by generating one or more excitation wavelengths sequentially, such as through the use of multiple alternating sources or lasers 206 and 208, or multiple exposures of the same lasers. The lasers 206 and 208 are coupled through an excitation light guide 210 to illuminate a common area, or tile, on the substrate 213 and sample 212. In response thereto, the sample 212 emits fluorescence which is collected by an objective lens 223.

Optionally, the light guide 210 (e.g., separate fiber optics) may be omitted or separate light guides 210 may be used based on the number, type and arrangement of sources or lasers 206 and 208. Optionally, more than two excitation wavelengths (e.g., 204 or 208) may be generated successively, such as by providing more than two lasers. Alternatively, a single laser may be used, but controlled to generate the desired number of multiple excitation wavelengths. As a further option, a plurality of excitation wavelengths may be generated using one or more lasers, while the number of lasers N and the number of excitation wavelengths M may differ (e.g., M<N). Optionally, the number of lasers may differ from the number of excitation events such as when multiple lasers are used simultaneously, or when a single laser is used multiple times. The AF module 218 includes a laser light source that generates a focusing beam 246. The focusing beam 246 is reflected by the dichroic mirror 216 onto the sample 212. The focusing beam 246 is then scattered and reflected from the sample 212, The scattered light, resulting from focusing beam 246, is collected by the objective lens 223. The scattered light, resulting from the focusing beam 246, propagates through the detection assembly 220 and is detected by one or more of detection cameras 236 and 238. The scattered light then foul's a basis for controlling focus, as described in more detail in international application publication no. WO 2003/060589, the contents of which are included herein by reference in their entirety.

The control module 211 is electrically connected to the excitation assembly 204 and controls activation and deactivation of the lasers 206 and 208 during excitation events. In the example of FIG. 2, a dashed line generally denoted at 214 illustrates an excitation beam that is channeled from the laser 206, through the light guide 210 and onto the sample 212 at a desired angle of incidence with respect to the surface or a reference plane on or within the substrate 213 holding the sample 212. A dashed line generally denoted at 215 illustrates an excitation beam that is channeled from the laser 208, through the light guide 210 and onto the sample 212 at a desired angle of incidence with respect to the surface or a reference plane on or within the substrate holding the sample 212. The control module 211 controls the excitation assembly 204 to generate an excitation light pattern throughout a sequence by synthesis analysis process. By way of example, the control module 211 may instruct the lasers 206 and 208 to generate excitation light at successive, non-overlapping periods of time. The laser 206 may supply a first pulse or burst of light as excitation beam 214 (e.g., at 532 nm) for a predetermined pulse duration, terminate the excitation beam 214, after which the laser 208 may supply a second pulse or burst of light as excitation beam 215 for a pulse duration and then terminate the excitation beam 215. In order to record two fluorophores with different wavelength emissions, each laser may be used once, or more than once on a single area (tile). For example, the sequence to record four different images in a single substrate tile may be a: wavelength one; filter one, b: wavelength one; filter two; c: wavelength two; filter three; d: wavelength two; filter four. The exposure time may be the same for each wavelength emission channel, or may be altered to control the intensity of the fluorescent signal recorded in the different channels. The exposure time may be the same for every cycle of sequencing, or may be increased throughout the sequencing run to compensate for any diminishing of the signal intensity as the cycles are performed.

Figure 3:
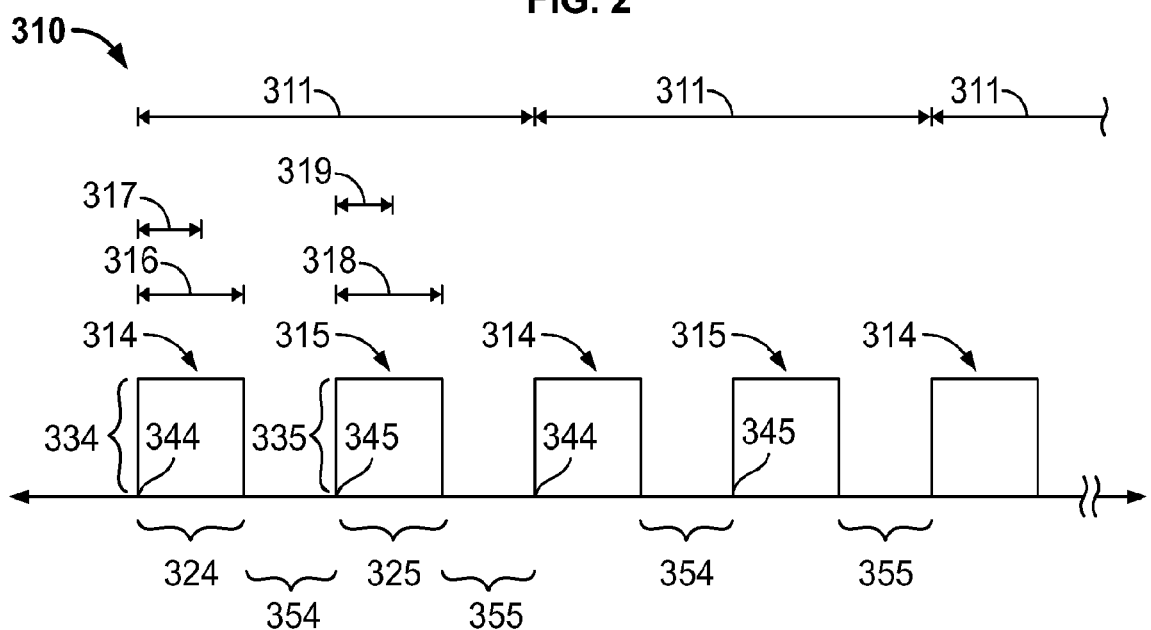
FIG. 3 illustrates a timing diagram for exemplary cycles within an analysis process in accordance with an embodiment.

FIG. 3 illustrates a portion of a sequence analysis process 310, where the horizontal axis denotes time. The analysis process 310 may be divided into illumination/detection cycles 311, where a series of operations are repeated during successive portions of each cycle 311. For example, each cycle 311 may include i) an excitation event 316, ii) a measurement phase 317, iii) an excitation event 318 and iv) a measurement phase 319. Multiple operations may be performed simultaneously and/or during partially or entirely overlapping time periods. For example, the excitation event 316 and measurement phase 317 may begin at substantially the same time and end at the same or different times. Similarly, the excitation event 318 and measurement phase 319 may begin at substantially the same time and end at the same or different times. The excitation event may be at least as long as the measurement event, but the sample may be illuminated for longer than the time takes to record an image on the detector. The exposure time for each tile typically ranges from 50 milliseconds-1 second, and it is understood that an excitation beam 214 or 215 may remain active for longer than an individual measurement event. The control module 211 controls both the laser sources 206 and 208, as well as cameras 236 and 238, so an exemplary series of control commands may be as follows; begin excitation, begin camera exposure, end camera exposure, end excitation. During the excitation events 316 and 318, the excitation assembly 204 optionally generates excitation beams 314 and 315, consecutively. During at least a portion of the measurement phases 317 and 319, the detection assembly 220 detects and records an amount and spectral pattern of fluorescence emitted by the sample 212. It is recognized that the duration of the measurement phases 317 and 319 is not necessarily co-extensive with the duration of the time period during which the sample 212 emits fluorescence. Instead, the sample 212 may emit fluorescence only during a short initial portion of the measurement phase 317 and 319, which corresponds to an initial portion of the excitation event 316 and 318.

It is recognized that the durations of the excitation events and measurement phases 316 to 319 are not illustrated to scale in FIG. 3. Instead, the durations of the excitation events 316 and 318 may be longer or shorter in relation to the durations of the measurement phases 317 and 319. As illustrated, the excitation events and measurement phases 316 to 319 overlap, such that the detection assembly 220 detects and measures fluorescence during the excitation event 316 and 318, while a corresponding one of the excitation beams 214 and 215 is being generated.

In the exemplary analysis process of FIG. 3, laser bursts 314 and 315 are delivered by the first and second excitation beams 214 and 215 successively, and in an interleaved manner, during the excitation events 316 and 318 repeatedly, during each cycle 311 throughout the analysis process 310. Each individual laser burst 314 and 315 has a laser burst duration 324 and 325, respectively, and amplitude 334 and 335. Leading edges 344 and 345 of laser bursts 314 and 315 are spaced apart to provide an inactive inter-burst interval 354 following each laser burst 314 before the next laser burst 315, and to provide an inactive inter-burst interval 355 following each laser burst 315 before the next laser burst 314. It is recognized that the burst durations 324 and 325, amplitudes 334 and 335, inter-burst intervals 354 and 355 are not illustrated to scale. Instead, the burst durations 324 and 325 may be very short, such as an impulse, as compared to the inter-burst intervals 354 and 355, while the amplitudes 334 and 335 may be quite substantial. Optionally, the inter-burst intervals 354 and 355 may be substantially zero such that the laser bursts 314 and 315 are continuous.

In the example of FIG. 3, the excitation events 316 and 318 are controlled to be non-overlapping temporally. The inter-excitation intervals 354 and 355 may be zero, the same or may differ from one another in duration. The inter-excitation interval 354 and 355 may remain constant through an analysis process 310 or may be varied from cycle 311 to cycle 311 throughout the analysis process 310. The excitation durations 324 and 325, are shown in FIG. 3 to be equal, but the burst duration 324 may vary from the excitation duration 325. Optionally, the excitation durations 324 and 325 may remain constant throughout an analysis process 310 or may be varied, such that the durations 324 and 325 during one cycle 311 of an analysis process 310 differ from the durations 324 and 325 during a later cycle 311 of the analysis process 310. The amplitudes 334 and 335 are shown FIG. 3 to be equal, but the amplitude 334 may vary from the amplitude 335. Optionally, the durations 324 and 325 may remain constant through an analysis process 310 or may be varied also between cycles 311. Also, the durations 324 and 325 may not equal the duration of the measurement phases 317 and 319. Instead, the laser bursts 314 and 315 may initiate before the beginning and terminate after the end of the measurement phases 317 and 319.

In the example of FIG. 2, the lasers 206 and 208 generate excitation light at different wavelengths that are chosen based on the wavelength spectrum of the fluorescent bases of interest that will potentially be present in the sample 212. In general, a number of bases may be labeled with a plurality of dyes or combinations of dyes, where each dye emits a corresponding known unique spectral pattern when illuminated with excitation light at a predetermined wavelength. For example, a number of bases (e.g., one or more) may be used that are each labeled with one or more dyes, where the dyes produce spectral patterns that are separately distinguishable along the wavelength spectrum. In a particular embodiment of the invention, each of the four bases is labeled with an individual fluorophore, such that the four bases can be spectrally distinguished, for example as described in international application publication no. WO 2007/135368, the contents of which are incorporated herein by reference in their entirety.

Figure 5:
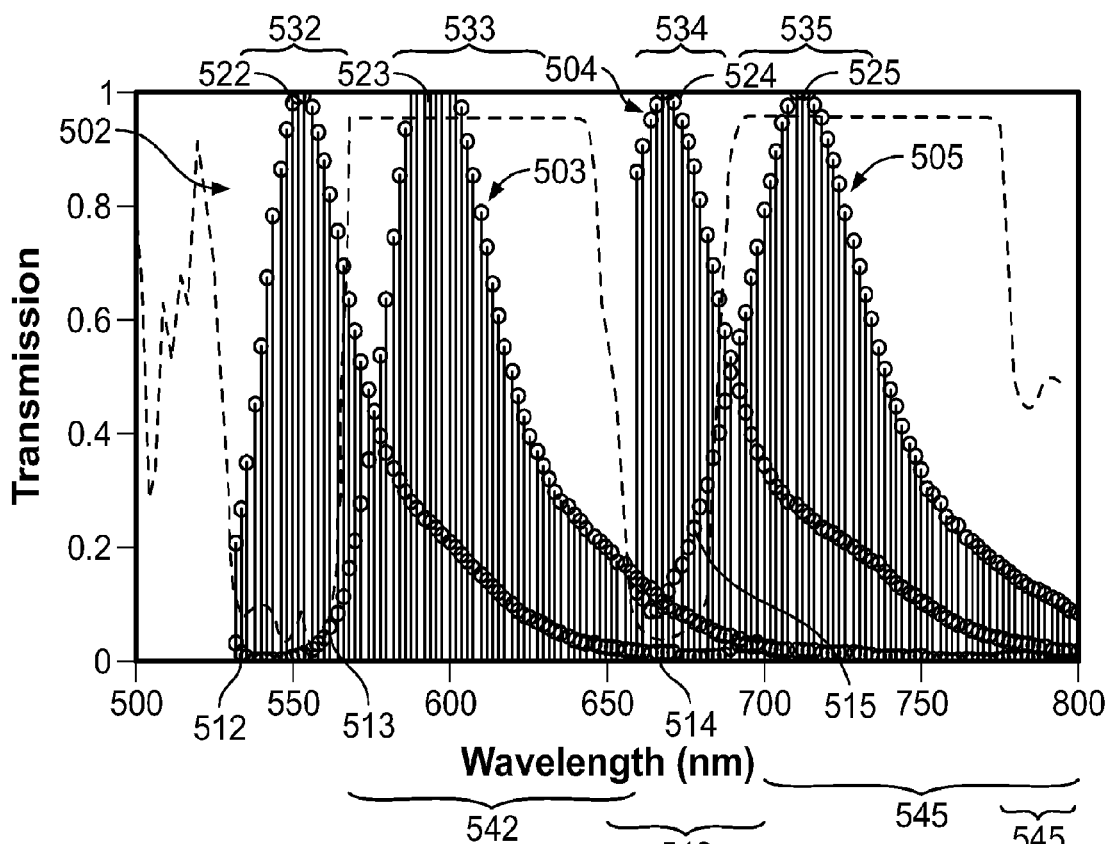
FIG. 5 illustrates an exemplary group of spectral band patterns for emission light that may be associated with a group of dyes used for labeling bases of interest in accordance with an embodiment.

FIG. 5 illustrates an exemplary group of spectral patterns 502-505 for emission light (e.g., fluorescence, luminescence, chemiluminescence, etc.) that may be associated with a group of dyes used for labeling bases of interest. In FIG. 5, the horizontal axis plots wavelength and the vertical axis plots transmission amplitude and transmittance on a normalized scale of 0 to 1. The spectral patterns 502-505 of emission light correspond to different dyes. Each individual excitation beam produces multiple spectral patterns of interest. For example, the fluorescent nucleotides G & T simultaneously emit fluorescence having spectral patterns 502 and 503 when illuminated with a single excitation beam having predetermined wavelengths (e.g., 532 nm), while fluorescent nucleotides A & C simultaneously emit fluorescence having spectral patterns 504 and 505 when illuminated with a single excitation beam having one or more different predetermined wavelengths (e.g., 660 nm). The wavelength(s) of the light used to excite dyes A & C differ from the wavelengths of the light used to excite dyes G & T.

The exemplary fluorescent nucleotides are denoted by the letters G, T, A & C. These letters correspond to the nucleotide bases attached to the fluorophores rather than the fluorophores themselves, and there is no significance in the order G, T, A, C. Any of the four fluorophores can be attached to any of the four bases within the scope of the invention. Each spectral pattern 502-505 includes a leading edge 512-515, a peak 522-525, a main body portion 532-535 and a tail portion 542-545, respectively. As shown in FIG. 5, while the tail portions 532-535 partially overlap one another, the peaks 522-525 are located at separate and discrete wavelengths along the wavelength spectrum, and the main body portions 532-535 encompass distributed substantially non-overlapping segments of the wavelength spectrum.

Returning to FIG. 2, downstream from the sample 212, a dichroic mirror 216 is located to receive the emission light 244 (e.g., fluorescence, luminescence, chemiluminescence, etc.) that is generated at the sample 212, such in response to the excitation beams 214 and 215, or in response to a chemical reaction when no excitation beams are used. The emission light 244 is comprised of multiple spectral bands denoted at 247-248. The spectral bands 247-248 generally differ from one another and may have different center wavelengths, mean wavelengths, median wavelengths, band widths, shapes and the like. The detection assembly 220 is located downstream of the dichroic mirror 216. The detection assembly 220 provides full field of view detection for the entire area of each tile of the substrate 212 measured by the objective lens 223.

The detection assembly 220 may include a further focusing component 224, a dichroic member 225, band pass filters 232 and 234, detection cameras 236 and 238, and a read out module 237. The focusing component 224 may for example be a tube lens, which allows the objective lens 223 to be infinity corrected. The detection assembly 220 is constructed entirely of non-moving parts that remain stationary and fixed with respect to one another, with respect to an axis of the optical system from the objective 223 and with respect to reflective and transmissive detection paths of the spectral bands 248 and 247, respectively.

In the example of FIG. 2, the spectral bands 247 and 248 correspond to fluorescence emitted by the sample 212 in response to excitation beams 214 and 215. The spectral bands 247 and 248 have different spectral patterns based upon the current dyes that are present on the substrate, and the excitation beam 214 or 215. By way of example, the spectral bands 247 and 248 may correspond to spectral patterns 502 and 503 (FIG. 5) when excitation beam 214 impinges upon the substrate 213. Alternatively, the spectral bands 247 and 248 may correspond to spectral patterns 504 and 505 (FIG. 5) when excitation beam 215 impinges upon the substrate 213. Spectral bands 247 and 248 are passed through the optional dichroic mirror 216 and into the detection assembly 220. The optional dichroic mirror 216 allows an autofocus module 218 to be entered into the optical system. Optionally, the autofocus module 218 and dichroic 216 may be removed entirely. Optionally, a filter 221 (e.g., band pass filter, notch filter, etc.) may be provided after the objective lens 223, in the space before the tube lens 224. The filter 221 blocks out excitation wavelengths. Optionally, the filter 221 may be provided further downstream (e.g., after the tube lens 224) or removed entirely.

In the example of FIG. 2, the optical component 222 constitutes a tube lens 224, although alternative structures may be used in combination with, or in place of, the tube lens 224. The tube lens 224 converges collimated emission light 244. The detection assembly 220 includes a dichroic member 225, such as a dichroic mirror 226, located downstream of the tube lens 224. The dichroic member 225 of FIG. 2 is formed entirely from a single dichroic mirror 226 having only a single incident surface that is coated to include multiple transmission or pass bands (e.g., at least two). The incident surface is coated to provide a transmissive/reflective spectrum comprising a desired combination of transmissive regions and reflective regions. The transmissive regions and reflective regions are separate and distinct from one another along the wavelength spectrum. Adjacent transmissive and reflective regions are immediately adjacent one another. The single incident surface of the dichroic mirror 226 may be oriented to form any desired angle of incidence with respect to an axis of the incoming emission light 244, such as for example 20-45°, or another suitable angle of incidence. The incident surface has a single common active area that receives both spectral bands 247 and 248. Fluorescence having spectral patterns 502 and 503 and fluorescence having spectral patterns 504 and 505 all impinge upon the common active area of the incident surface of the dichroic mirror 226. The dichroic mirror 226 reflects spectral band 248 and passes spectral band 247 there through. The passed spectral band 247 is directed along a transmissive detection path onto a band pass filter 232, while the spectral band 248 is reflected along a reflective detection path onto a band pass filter 234.

Optionally, the dichroic member 225 may comprise multiple dichroic mirrors or equivalent structures arranged along the optical path and configured to provide a desired number of transmission or pass bands. Optionally, the dichroic member 225 may be moved upstream of the tube lens 224 and multiple separate tube lenses 224 may direct light onto the corresponding detection cameras 236 and 238. The band pass filters 232 and 234 block high and low spectral content of the incoming spectral bands 247 and 248, respectively, and pass the portions of the spectral bands 247 and 248 within the upper and lower limits of the pass bands. The limits of the pass bands may be set to sharpen edges of spectral patterns, block noise, block scatter, block excitation light and the like. Optionally, the band pass filters 232 and 234 may be removed entirely and replaced with an appropriate filter 221. The passed portions of the spectral bands 247 and 248 are directed onto corresponding detection cameras 236 and 238.

The band pass filters 232 and 234, and detection cameras 236 and 238 may be oriented at various angles of incidence with respect to the transmissive and reflective paths and with respect to one another. For example, the detection cameras 236 and 238 may be oriented in a perpendicular geometry or acute angular relation with one another (e.g., 90°, etc.).

The detection cameras 236 and 238 detect the spectral bands 247 and 248, respectively, and provide electrical detection signals 241 and 243 to a readout module 237, for example a computer. The electrical signals can be provided to the readout module 237 continuously or at discrete times during the measurement phases 317 and 319 (FIG. 3). The electrical detection signals 241 and 243 may be analog or digital signals representing an amount of emission energy (fluorescent or otherwise) measured by the detection cameras 236 and 238. The detection cameras 236 and 238 may output the detection signals 241 and 243 as continuous signals representative of an instantaneous measurement. Alternatively, the detection cameras 236 and 238 may output the detection signals 241 and 243 as a series of period signals representative of discrete measurements taken at discrete times. The readout module 237 records the detection signals 241 and 243 and provides a series of images 239 representative of the emission light that was detected by each of the detection cameras 236 and 238. For example, the readout module 237 may provide a single image for each detection camera 236 and 238 during each measurement phase. Alternatively, the readout module 237 may provide a series of images for each detection camera 236 and 238 during each measurement phase.

Figure 6:
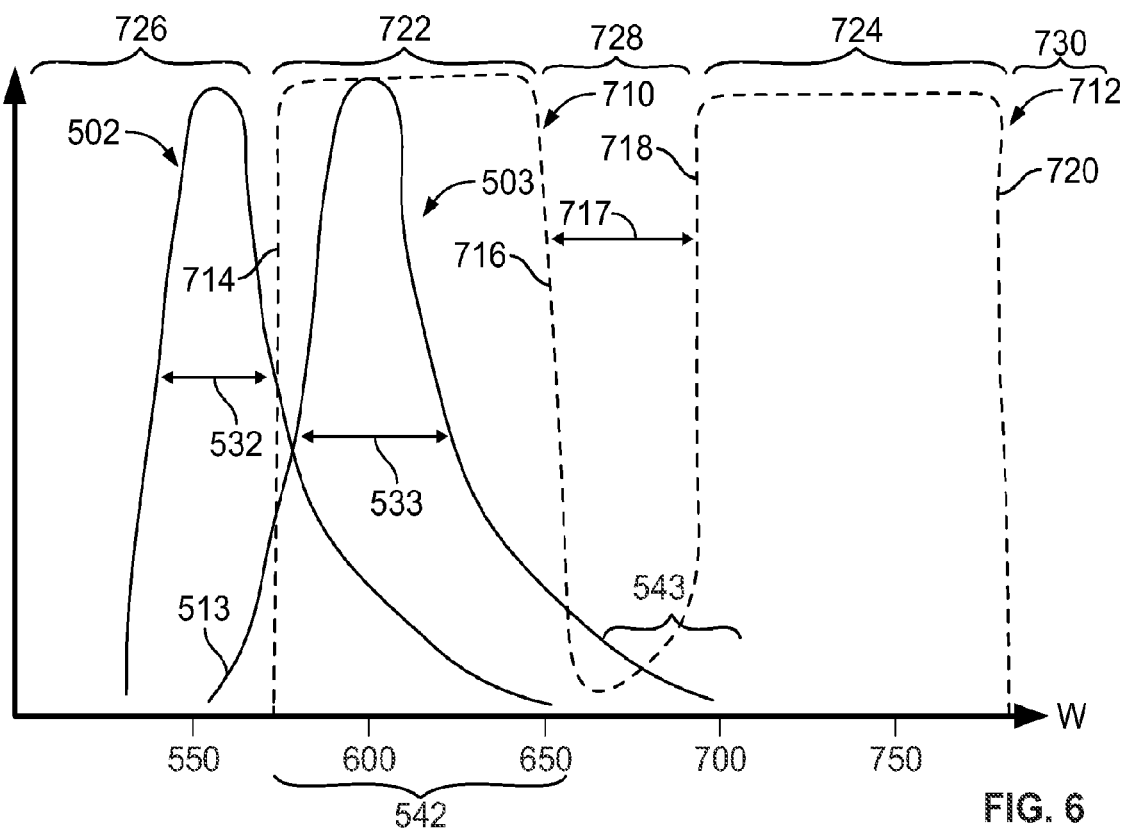
FIG. 6 illustrates an exemplary transmission/reflection characteristic that a dichroic member may be configured to exhibit, along with exemplary fluorescence spectral emission patterns, in accordance with an embodiment.
Figure 7:
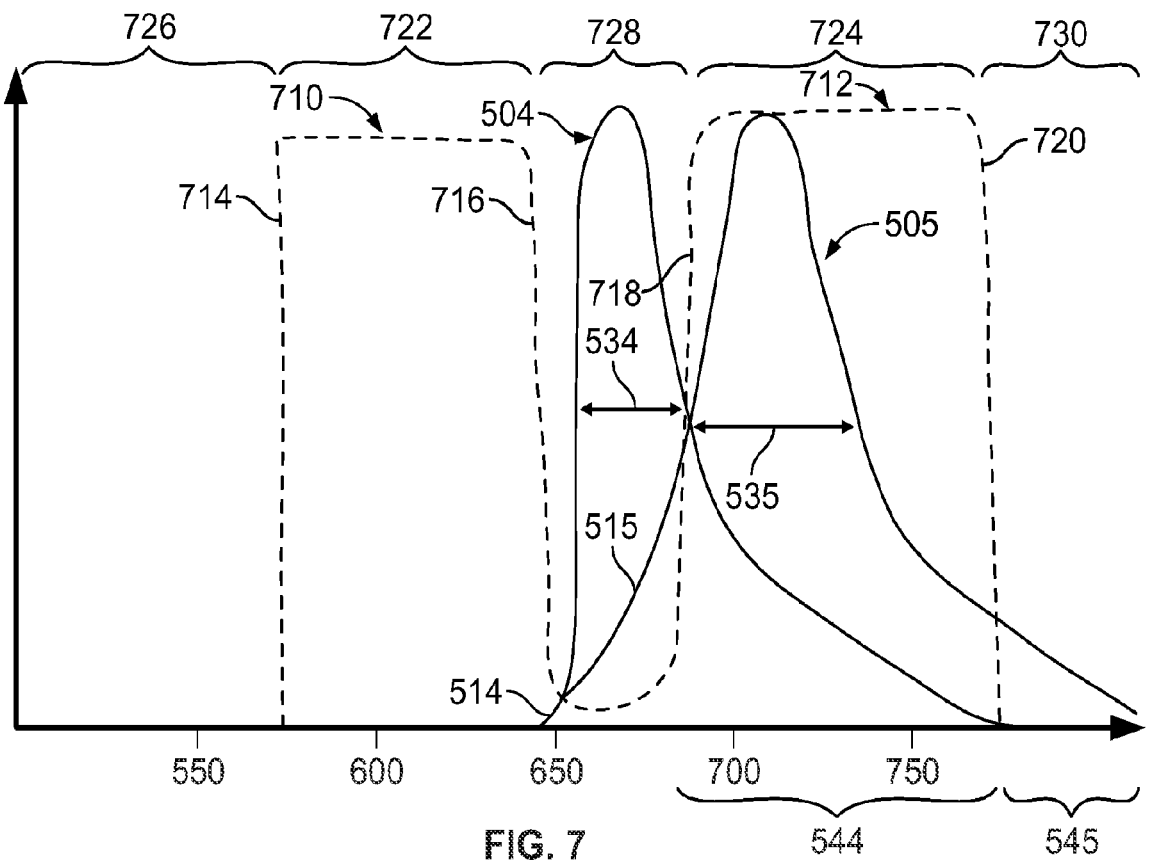
FIG. 7 illustrates the exemplary transmission/reflection characteristic of Figure S, along with additional exemplary fluorescence spectral emission patterns.

Next, the operation of the excitation and detection system 202 is described, with respect to FIGS. 6 and 7, in connection with an exemplary cycle of an analysis process. For the example of FIGS. 6 and 7, it is assumed that the sample 212 includes one or more bases with fluorescent nucleotides G, T, A & C that emit fluorescence having the spectral patterns 502-505 illustrated in FIG. 5.

FIGS. 6 and 7 illustrate an exemplary transmission/reflection characteristic that the dichroic member 225 may be configured to exhibit, along with the spectral patterns 502-505 of FIG. 5. The dichroic member 225 may be configured to exhibit different transmission/reflection characteristics based on the expected spectral emission patterns of other dyes that may be used. The horizontal axes in FIGS. 6 and 7 represent wavelength, while the vertical axes represent emission or transmissivity. As shown in each of FIGS. 6 and 7, the dichroic member 225 is constructed with at least two pass bands 710 and 712. The pass band 710 includes cutoffs at transmittance lower and upper limits 714 and 716, while the pass band 712 includes lower and upper limits 718 and 720. The pass bands 710 and 712 are separated from one another along the wavelength spectrum such that the upper limit 716 of the lower pass band 710 is spaced apart by a desired wavelength range (denoted at 717) below the lower limit 718 of the upper pass band 712. The dichroic member 225 exhibits at least a pair of transmissive regions 722 and 724 that are separated by a reflective region 728 and bound by outer reflective regions 726 and 730. Fluorescent incident light, having wavelengths within the transmissive regions 722 and 724, is passed through the dichroic member 225 onto band pass filter 232 and detection camera 236. Incident light, having wavelengths within the reflective regions 726, 728 and 730, is reflected by the dichroic member 225 onto band pass filter 234 and detection camera 238, and hence the two signals are recorded simultaneously.

FIG. 6 corresponds to the measurement phase associated with a first excitation event when the laser 206 generates the excitation beam 214. FIG. 7 corresponds to the measurement phase associated with a second excitation event when the laser 208 generates the excitation beam 215. During the first excitation event, fluorescence is generated having the spectral patterns 502 and 503. During the second excitation event, fluorescence is generated having the spectral patterns 504 and 505.

Although the example is shown with two consecutive excitations with different wavelengths, the use of the dual band pass dichroic means that both excitation events can be performed simultaneously, using both beams 214 and 215 at the same time. In this embodiment, the optical system may comprise four detection cameras rather than the two shown in FIG. 2, although the concept of using two cameras and two excitation wavelengths is within the scope of the invention. For the consecutive excitation events, the order of wavelength illuminations is not relevant, and the laser sources may be used in any order; e.g., spectral patterns 504 and 505 may be generated either before or after spectral patterns 502 and 503.

Following initiation of excitation beam 214, the sample (when containing fluorescent nucleotides G, T, A and C discussed above) emits fluorescence having the spectral patterns 502 and 503 (as shown in FIG. 6). In the case where wavelengths 214 and 215 are used simultaneously, spectral patterns 502-505 are generated simultaneously. The portion of the spectral pattern 502 (shown associated with dye G) that falls within the reflective region 726 is reflected by the dichroic mirror 226 onto the band pass filter 234. The portion of the spectral pattern 503 (shown associated with dye T) that falls within the region 722 is passed through the dichroic mirror 226 and directed onto the band pass filter 232. As is evident in FIG. 6, the amount of energy associated with the leading edge 513 of the spectral pattern 503 that falls within the reflective region 726 is relatively small in comparison to the amount of energy within the main body portion 532 of the spectral pattern 502 that is reflected by the dichroic mirror 226. Hence, the majority of the signal detected by camera 238 corresponds to spectral pattern 502 (the 'G' signal), and the leading edge 513 does not detrimentally impact the accuracy of the detection camera 238.

The signal detected by camera 236 will comprise components deriving from both tail portion 542 of spectral pattern 502, and the main body portion 533 of spectral pattern 503. The tail portion 542 and main body portion 533 may be of similar intensity without compromising the accuracy of determining whether the identity of the object is 'T' or 'G', due to the detection of all objects of signal 'G' on camera 236.

The leading edge 513 and the tail portion 543 of the spectral pattern 503 fall within reflective regions 726 and 728, respectively, and thus are reflected by the dichroic mirror 226. However, as explained above, the amount of energy associated with the leading edge 513 is relatively small in comparison to the amount of energy within the main body portion 532 of the spectral pattern 502 that is reflected by the dichroic mirror 226. The tail portion 543 is removed using the band pass filter 234, and hence, the leading edge 513 and tail portion 543 do not detrimentally impact the accuracy of the detection camera 238. The dichroic mirror 226 lets through all the light in pass bands 710 and 712. As an option, the band pass filters 232 and 234 may be configured to block partially the unwanted leading edges 513 and 515 and tail portions 543 and 545, before reaching the detection cameras 236 and 238.

Turning to FIG. 7, following initiation of the excitation beam 215, the sample 212 emits fluorescence having the spectral patterns 504 and 505 (as shown in FIG. 7). The main body portion 534 of the spectral pattern 504 (shown associated with dye A) that falls within the reflective region 728 is reflected by the dichroic mirror 226 onto the band pass filter 234. The main body portion 535 of the spectral pattern 505 (shown associated with dye C) that falls within the transmissive region 724 is passed through the dichroic mirror 226 and directed onto the band pass filter 232. As is evident in FIG. 7, the amount of energy associated with the leading edge 515 of the spectral pattern 505 that falls within the reflective region 728 is relatively small in comparison to the amount of energy within the main body portion 534 of the spectral pattern 504 that is reflected by the dichroic mirror 226. Hence, the leading edge 515 does not detrimentally impact the accuracy of the detection camera 238.

The signal detected by camera 236 will comprise components deriving from both the main body portion 535 of spectral pattern 505, and the tail portion 544 of spectral pattern 504. The main body portion 535 and tail portion 544 may be of similar intensity without compromising the accuracy of determining whether the identity of the object is 'A' or 'C', due to the detection of all objects of signal 'A' on camera 236.

Similarly, it is apparent that the leading edge 515 and the tail portion 545 of the spectral pattern 505 falls within reflective regions 728 and 730, respectively, and thus are reflected by the dichroic mirror 226. However, as explained above, the amount of energy associated with the leading edge 515 and tail portion 545 is relatively small in comparison to the amount of energy within the main body portion 534 of the spectral pattern 504 that is reflected by the dichroic mirror 226. The tail portion 545 is removed using the band pass filter 234, and hence, the leading edge 515 and tail portion 545 do not detrimentally impact the accuracy of the detection camera 238. The dichroic mirror 226 lets through all the light in pass bands 710 and 712. As an option, the band pass filters 232 and 234 may be configured to block partially the unwanted leading edges 513 and 515 and tail portions 543 and 545, before reaching the detection cameras 236 and 238.

In the example of FIGS. 6 and 7, the lower limits 714 and 718 are used as transmittance cut off frequencies to discriminate between closely spaced spectral patterns, whereas the upper limits 716 and 720 are not. Optionally, the transmissive regions 722 and 724 could be switched with reflective regions 726 and 728, respectively, to pass spectral patterns 502 and 504, and reflect spectral patterns 503 and 505. As a further option, additional spectral patterns may be used such that the lower and upper limits 714, 716, 718 and 720 could all be used to discriminate between adjacent spectral patterns (e.g., when 5 or 8 dyes are used to generate 6 or 8 spectral patterns).

Figure 8:
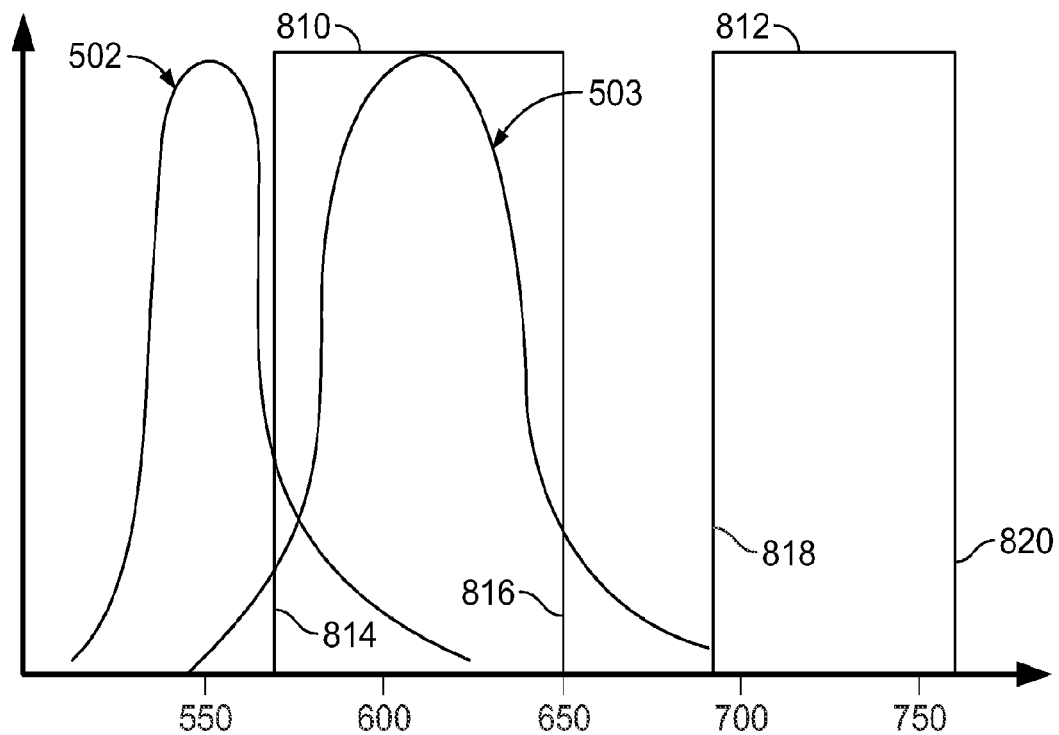
FIG. 8 illustrates exemplary filter characteristics of band pass filters in accordance with an embodiment, along with exemplary fluorescence spectral emission patterns.
Figure 9:
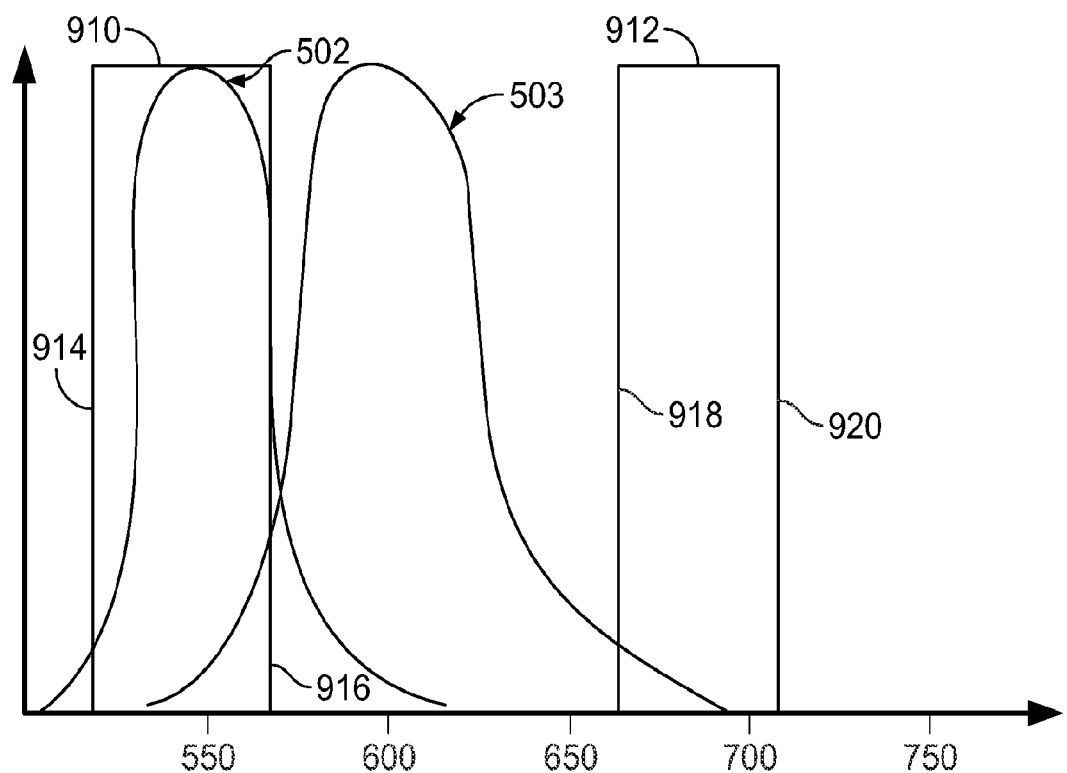
FIG. 9 illustrates exemplary filter characteristics of band pass filters in accordance with an embodiment, along with exemplary fluorescence spectral emission patterns.
Figure 10:
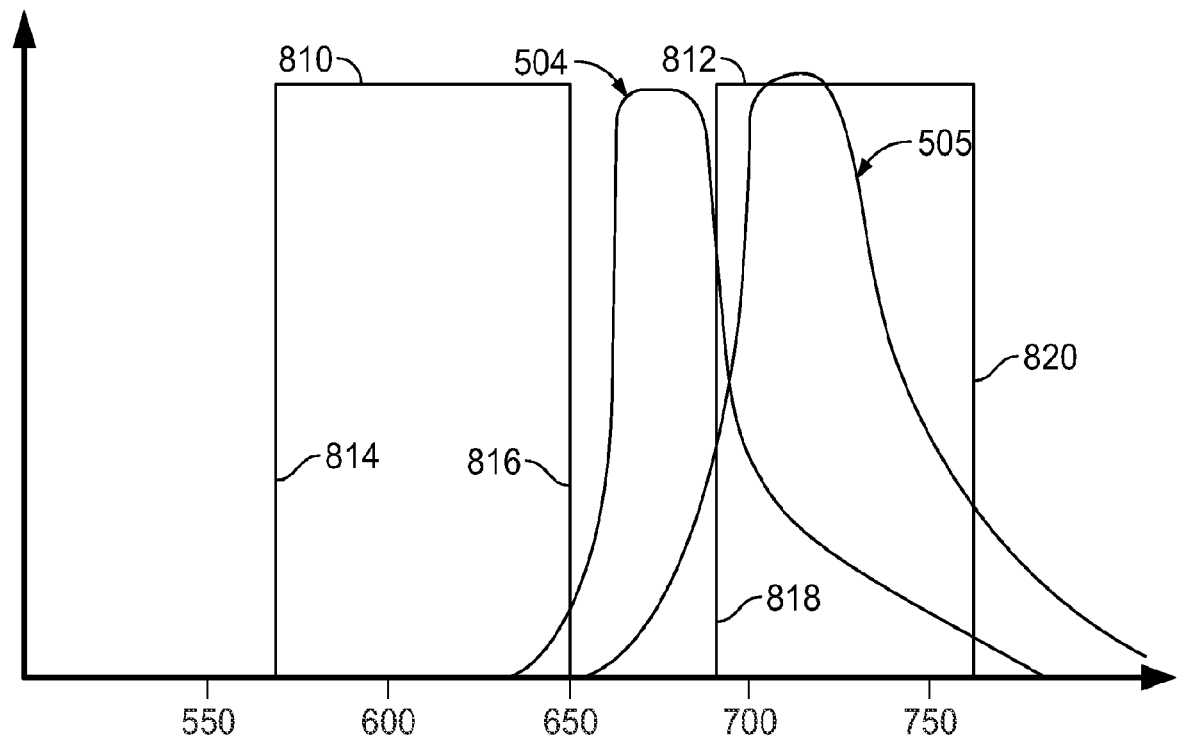
FIG. 10 illustrates exemplary filter characteristics of a band pass filters in accordance with an embodiment, along with exemplary fluorescence spectral emission patterns.
Figure 11:
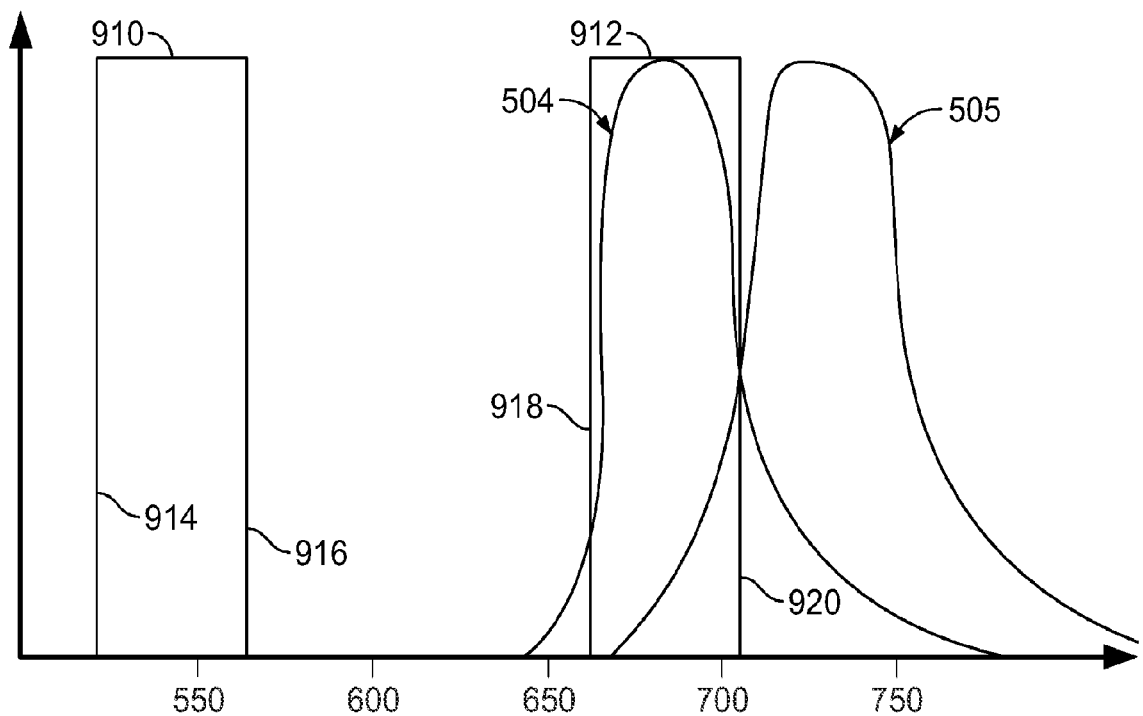
FIG. 11 illustrates exemplary filter characteristics of a band pass filters in accordance with an embodiment, along with exemplary fluorescence spectral emission patterns.

FIGS. 8 and 10 illustrate exemplary filter characteristics that the band pass filters 232 may be configured to exhibit when used with the spectral emission patterns 502-505 of FIG. 5. FIGS. 9 and 11 illustrate exemplary filter characteristics that the band pass filters 234 may be configured to exhibit when used with the spectral emission patterns 502-505 of FIG. 5. The horizontal axes in FIGS. 8-11 represent wavelength, while the vertical axes represent transmissivity.

As shown in FIGS. 8 and 10, the band pass filter 232 is constructed to have multiple pass bands 810 and 812. The pass band 810 includes lower and upper limits 814 and 816, while the pass band 812 includes lower and upper limits 818 and 820. The pass bands 810 and 812 are separated from one another along the wavelength spectrum such that the upper limit 816 of the lower pass band 810 is spaced apart by a desired wavelength range (denoted at 817) below the lower limit 818 of the upper pass band 812. Incident light, having wavelengths within the pass bands 810 and 812, is passed through the filter 232 onto detection camera 236. Emission incident light, having wavelengths outside the pass bands 810 and 812, is blocked. Thus, as shown in FIGS. 8 and 10, the majority of the emission light having spectral patterns 503 and 505 are conveyed through the filter 232, while the regions of the emission light having spectral patterns 502 and 504 are blocked.

As shown in FIGS. 9 and 11, the band pass filter 234 is constructed to have multiple pass bands 910 and 912. The pass band 910 includes lower and upper limits 914 and 916, while the pass band 912 includes lower and upper limits 918 and 920. The pass bands 910 and 912 are separated from one another along the wavelength spectrum such that the upper limit 916 of the lower pass band 910 is spaced apart by a desired wavelength range from the lower limit 918 of the upper pass band 912. Emission incident light, having wavelengths within the pass bands 910 and 912, is passed through the filter 234 onto detection camera 238. Emission incident light, having wavelengths outside the pass bands 910 and 912, is blocked. Thus, as shown in FIGS. 9 and 11, the majority of the fluorescence having spectral patterns 502 and 504 are conveyed through the filter 234, while the majority of the fluorescence having spectral patterns 503 and 505 are blocked.

In accordance with at least one embodiment described the multi-pass band dichroic member affords the technical effect of separating the spectral patterns 502 and 503 for delivery to different detection cameras utilizing a detection assembly having non-moving parts that remain stationary and fixed throughout the analysis process. Further, in accordance with at least one embodiment, the multi-pass band dichroic member affords the technical effect that spectral patterns 502 and 504 may be excited with different excitation beams while being imaged on the same detection camera.

As explained above, more than two excitation wavelengths may be used. Multiple excitation wavelengths can be present in a single excitation beam, such as a beam of white light, or each wavelength can be present in a separate beam, such as a laser beam. It may be equally possible to excite the multiple fluorophores using a single fixed laser. Such systems for exciting multiple fluorophores using a single laser may also include the use of energy transfer labels from a single donor to different acceptors, or the use of labels with different Stokes shifts, such as Quantum dots or similar microparticles.

Figure 12:
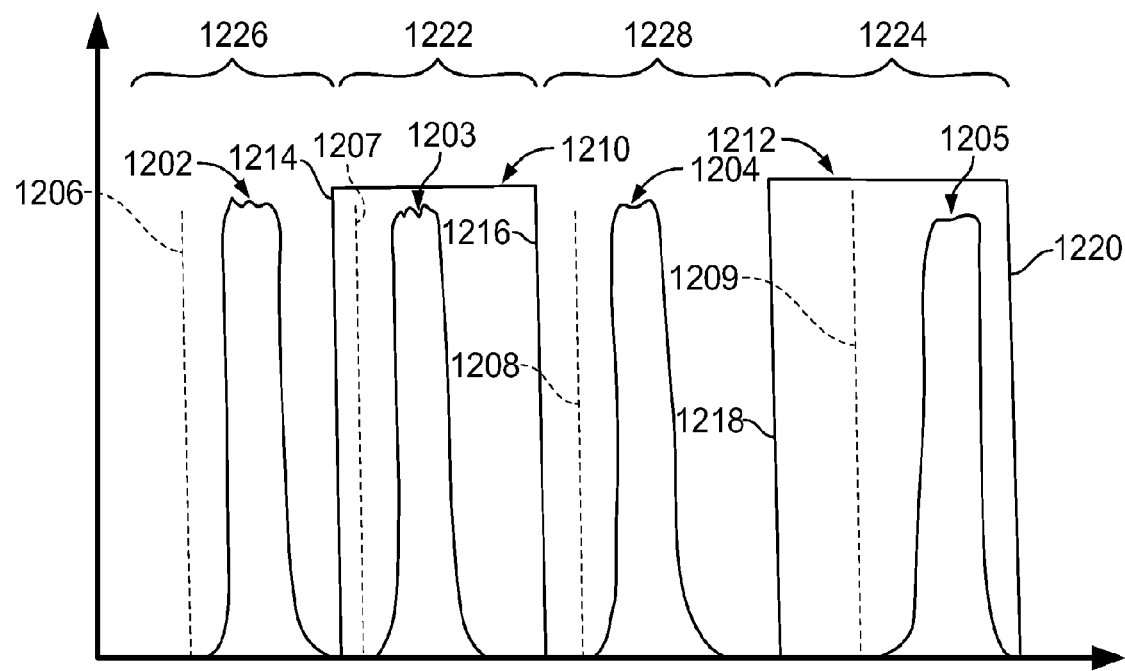
FIG. 12 illustrates a filter characteristic, excitation beams and spectral emission patterns formed in accordance with an alternative embodiment.

FIG. 12 illustrates an alternative embodiment in which a transmission/reflection characteristic for a single dichroic mirror 226 may be configured for use with four separate excitation wavelengths 1206-1209. The excitation wavelengths 1206-1209 produce fluorescence with the spectral patterns 1202-1205, respectively. The horizontal axis represents wavelength, while the vertical axis represents transmittance. The dichroic mirror 226 is constructed with at least two pass bands 1210 and 1212. The pass band 1210 includes lower and upper limits 1214 and 1216, while the pass band 1212 includes lower and upper limits 1218 and 1220. Fluorescence with spectral patterns 1203 and 1205 within the transmissive regions 1222 and 1224 are passed through the dichroic mirror 226 onto band pass filter 232 and detection camera 236. Fluorescence with spectral patterns 1202 and 1204 within the reflective regions 1226 and 1228 are reflected by the dichroic mirror 226 onto band pass filter 234 and detection camera 238.

The excitation beams 1206-1209 may be produced sequentially or in combinations (e.g., pair 1206 and 1208, then pair 1207 and 1209). For example, fluorescence may be generated having the spectral emission patterns 1202 and 1203 for a period of time following the excitation beams 1206 and 1207, but before initiation of the excitation beams 1208 and 1209. Fluorescence may be generated having the spectral patterns 1204 and 1205 for a period of time following the excitation beams 1208 and 1209.

Optionally, the excitation assembly 204 may be controlled to generate multiple excitation beams simultaneously, where each excitation beam has a distinct wavelength. As explained above, the labels may be configured to emit fluorescence with multiple spectral patterns in response to each wavelength of excitation beam.

Figure 17:
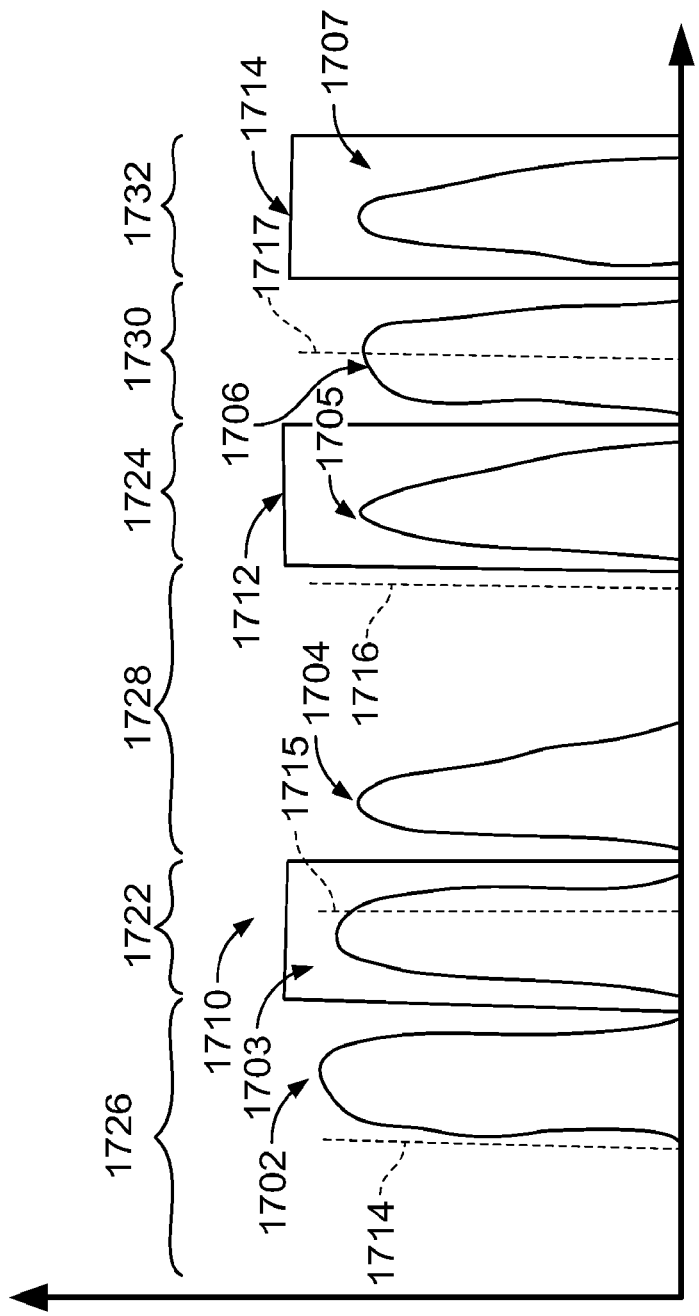
FIG. 17 illustrates a filter characteristic, excitation beams and spectral emission patterns formed in accordance with an alternative embodiment.

FIG. 17 illustrates an alternative embodiment in which a transmission/reflection characteristic for a single dichroic mirror may be configured for use with four excitation beams 1714-1717 that are generated simultaneously. The horizontal axis represents wavelength, while the vertical axis represents transmittance. The excitation beams 1714 and 1715 collectively produce fluorescence with the spectral patterns 1702, 1703 and 1704, respectively. The excitation beams 1716 and 1717 collectively produce fluorescence with the spectral patterns 1705, 1706 and 1707. In the example of FIG. 17, a group of N excitation wavelengths (e.g., 1714-1715) are used to produce a group of M spectral patterns (e.g., 1702-1704). The dichroic mirror 226 is constructed with at least three pass bands 1710, 1712 and 1714. Fluorescence with spectral patterns 1703, 1705 and 1707 within the transmissive regions 1722, 1724 and 1732 are passed through the dichroic mirror 226 onto band pass filter 232 and detection camera 236. Fluorescence with spectral patterns 1702, 1704 and 1706 within the reflective regions 1726, 1728 and 1730 are reflected by the dichroic mirror 226 onto band pass filter 234 and detection camera 238. The excitation wavelengths 1714 to 1717 can be produced, simultaneously, sequentially or in combinations. Optionally, the excitation wavelengths 1715 and 1717 may be removed entirely, and only excitation wavelengths 1714 and 1716 illuminate a sample to produce the illustrated spectral patterns 1702 to 1707.

Devices for Detecting Fluorescence

The detection devices 236 and 238 may be, for example photodiodes or cameras. In some embodiments herein, the detection camera can comprise a 1 mega pixel CCD-based optical imaging system such as a 1002×1004 CCD camera with 8 μm pixels, which at 20× magnification can optionally image an area of 0.4×0.4 mm per tile using a laser spot size of 0.5×0.5 mm (e.g., a square spot, or a circle of 0.5 mm diameter, or an elliptical spot, etc.). The detection cameras can optionally have more or less than 1 million pixels, for example a 4 mega pixel camera can be used. In many embodiments, it is desired that the readout rate of the camera should be as fast as possible, for example the transfer rate can be 10 MHz or higher, for example 20 or 30 MHz. More pixels generally mean that a larger area of surface, and therefore more sequencing reactions or other optically detectable events, can be imaged simultaneously for a single exposure. In particular embodiments, the CCD camera/TIRF lasers herein are capable of collecting about 6400 images to interrogate 1600 tiles (since images are optionally done in 4 different colors per cycle using combinations of filters, dichroics and detectors as described herein. For a 1 Mega pixel CCD, certain images optionally can contain between about 5,000 to 50,000 randomly spaced unique nucleic acid clusters (i.e., images upon the flowcell surface). At an imaging rate of 2 seconds per tile for the four colors, and a density of 25000 clusters per tile, the systems herein can optionally quantify about 45 million features per hour. At a faster imaging rate, and higher cluster density, the imaging rate can be significantly improved. For example, at the maximum readout rate of a 20 MHz camera, and a resolved cluster every 20 pixels, the readout can be 1 million clusters per second. As described herein, the light can be split to simultaneously image two colors onto two cameras, or even four colors onto four cameras. If four cameras are used in parallel, it is thus possible to sequence 1 million bases per second, or 86.4 billion bases per day.

There are at least two ways of splitting up the optical signals for a two camera system. If two lasers are used, there may be a red excitation and a green excitation, with half the emission light split towards each camera. Alternatively both lasers may be used in both illumination cycles, and the light may pass through a suitable dichroic mirror 226, so sending the red light in one direction, and the green light in a different direction. Such system prevents the signal losses associated with beam splitting, but does mean that two of the dyes are exposed to the laser before their intensity is recorded. In some such embodiments, the excitation blocker can comprise a dual notch filter (e.g., 532 and 660 nm). In such an embodiment, band pass filters 232 and 234 are typically rotated between images in order to measure region 722 during a first excitation event, and 726 on a second excitation event of the same wavelength onto the same camera. Embodiments of the present invention described in the current application avoid the use of filter rotation by using a stationary, dual band pass dichroic member, which means that rather than performing two consecutive illuminations and measurements in which both illuminations require both wavelengths at each illumination, the consecutive illuminations can be performed using a single wavelength per illumination. In accordance with certain embodiments, the advantages include a reduction in the time a sample is illuminated leading to reduced photobleaching that would otherwise cause the signal of the fluorescent signal to be reduced before the image is recorded. A further advantage is the avoidance of moving parts in the optical detection system.

A "tile" herein is functionally equivalent to the image size mapped onto the substrate surface. Tiles can be, e.g., 0.33 mm×0.33 mm, 0.5 mm×0.5 mm, 1 mm×1 mm, 2 mm×2 mm etc, although the size of the tile will depend to a large extent on the number and size of pixels on the camera and the desired level of magnification. Also, it will be appreciated that the tile does not have to equal the same size or shape as the illumination footprint from the laser (or other light source), although this can be advantageous if the minimization of photobleaching is desired.

As stated previously, in the various embodiments herein, the camera/laser systems collect fluorescence from 4 different fluorescent dyes (i.e., one for each nucleotide base type added to the flowcell).

Figure 13:
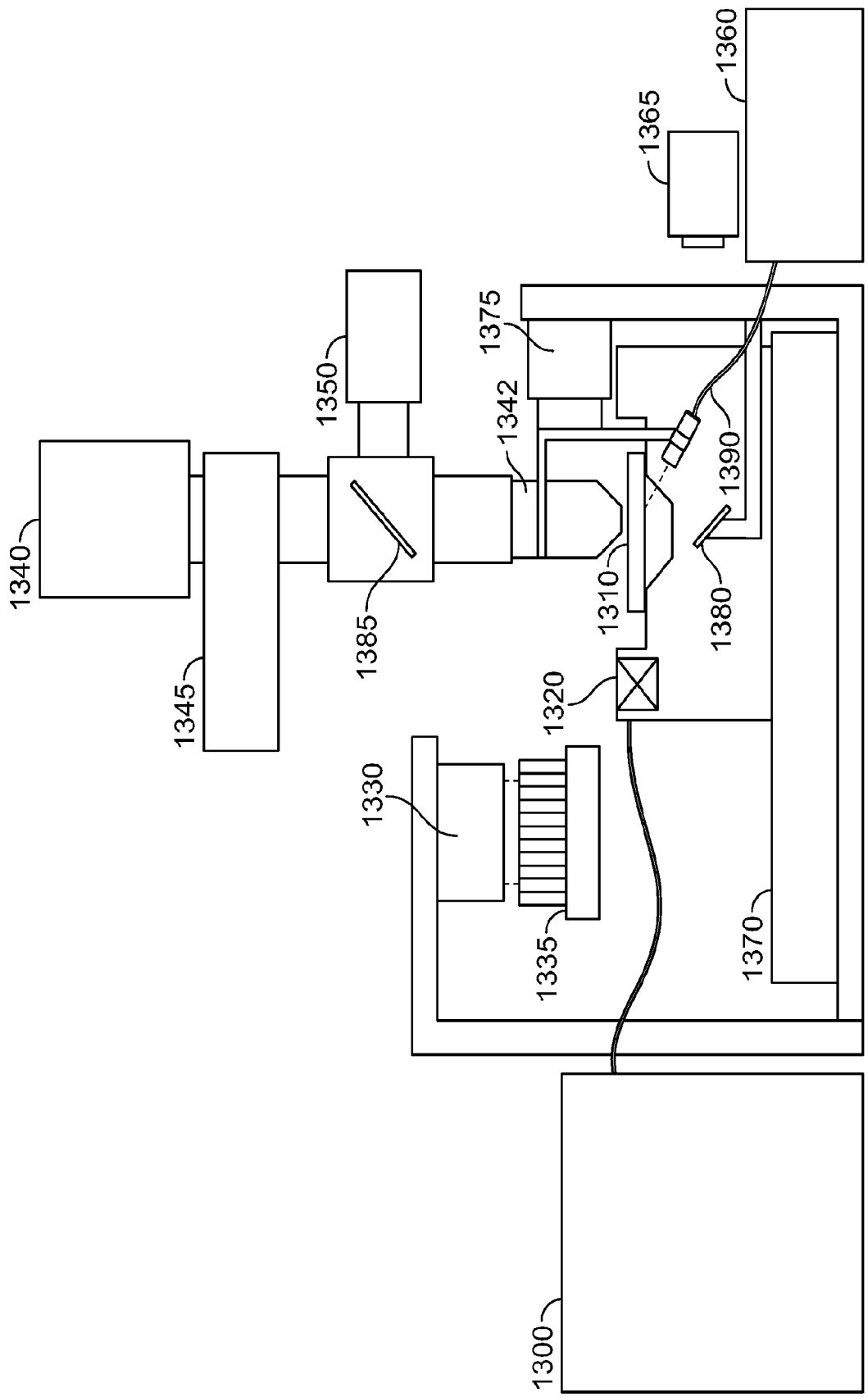
FIGS. 13-16 illustrate various optional configurations of cameras, light sources, and other components formed in accordance with alternative embodiments.

FIGS. 1 and 13-16 show alternative embodiments of the cameras and lasers of the present invention, including a backlight design, a TIRF Imaging configuration, a laser focusing configuration, a white-light viewing configuration, and an alternative laser focusing design. The white light excitation source is optional, and can be used as well as, or instead of, the excitation lasers. FIG. 1 shows the backlight design system whilst recording an image in the TIRF imaging configuration. The configuration in FIG. 1 for the TIRF imaging is optionally a configuration of the backlight design set-up shown in FIG. 13. In FIG. 1, one of the two lasers (in laser assembly 160) is used to illuminate the sample (in flowcell 110), and a single one of the four emission filters (in filter switching assembly 145) is selected to record a single emission wavelength and to cut out any stray laser light. During imaging, both focus laser (150) and optional white light lamp (165) can be prevented from illuminating the sample either by being blocked with a shutter or switched off. Laser illumination 101 and illumination from the flowcell up through the lens objective and camera 102 are also shown. FIG. 13 shows all the components of the system in the backlight design but without the specific TIRF imaging configuration. Cf. FIGS. 1 and 13. Thus FIG. 13 shows: fluid delivery module 1300, flowcell 1310, waste valve 1320, temperature actuator 1330, heating/cooling component (e.g., Peltier) 1335, camera (e.g., CCD camera) 1340, objective lens 1342, filter switching assembly 1345, focusing laser assembly 1350, excitation lasers assembly 1360, low watt lamp 1365, precision XY stage 1370, focus (z-axis) device 1375, mirror 1380, "reverse" dichroic 1385, and laser fiber optic 1390.

Figure 14:
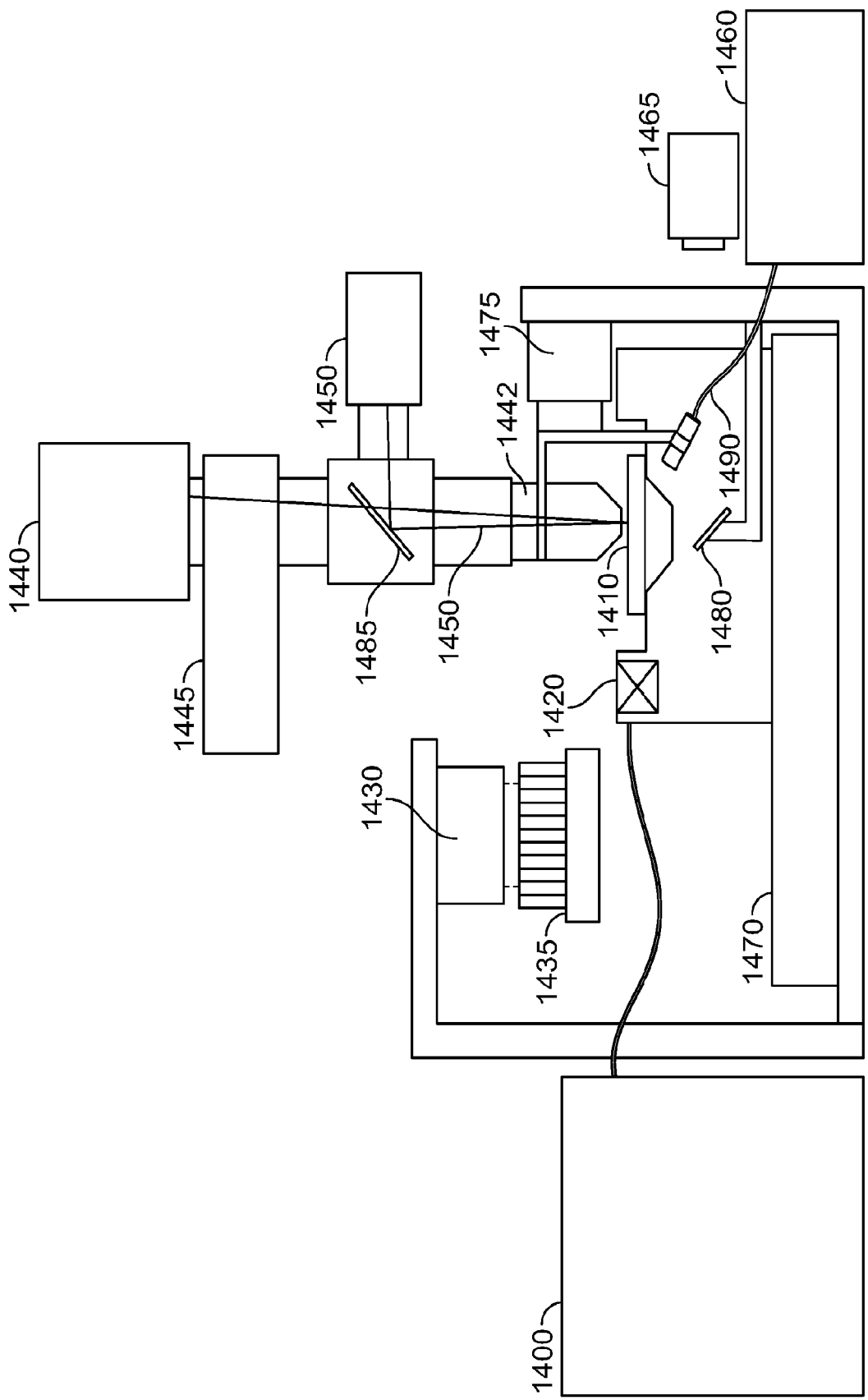

FIG. 14 shows a similar system as that in FIG. 1, but in the laser focusing configuration where the excitation lasers (in laser assembly 1460) and optional white light 1465 are switched off. Focusing laser 1450 is on and shines into the system, hits beam splitter 1485 (e.g., a pick-off mirror ×1% beam splitter) which direct a faint beam 1420 down the objective to hit a small spot on the sample (in flowcell 1410). The reflected light from the sample returns up objective (1442) through an empty slot in filter wheel switching assembly 1445 and is imaged by CCD camera 1440. The position of the spot on the camera is used to ensure the sample is at the right distance from the objective, and therefore the image will be in focus. The numbering of the elements in FIG. 14 is similar to that of the elements in FIG. 13, but numbered as "14" rather than "13," e.g., 1460 corresponds to a similar element as 1360, etc. In embodiments where the band pass filters are fixed, the autofocus laser may be a suitable wavelength to pass through one of the filters rather than using an empty slot in the filter switching assembly. The small size and low intensity of the spot prevents damage to the sample.

Figure 15:
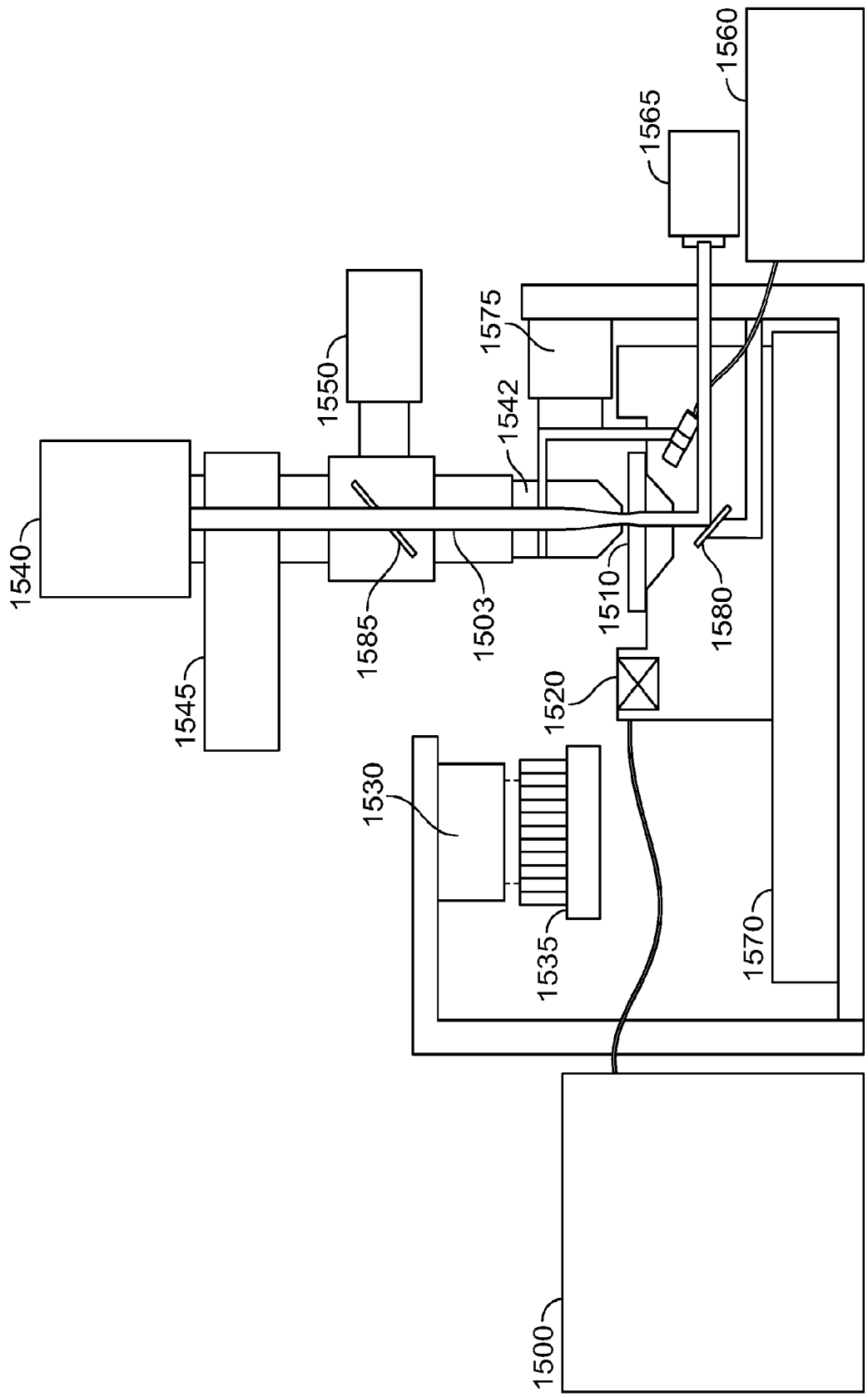
Figure 16:
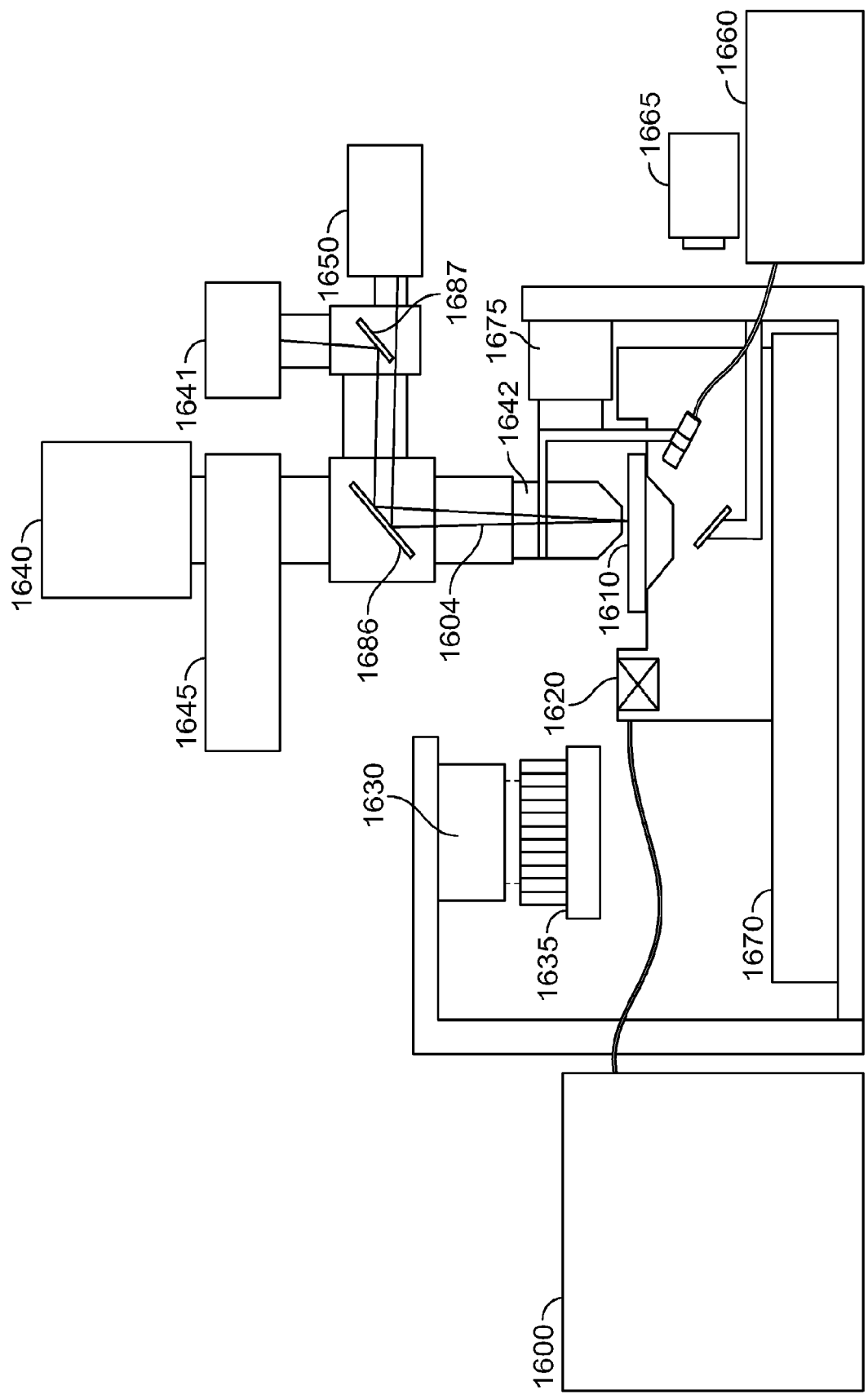

FIG. 15 shows the optional white light viewing configuration, where focus laser 1550 and illumination lasers 1560 are off. In such configuration the white light from low watt lamp 1565 goes into the system as beam 1503 and is imaged directly on the camera. Here too, the numbering of elements, except for beam 1503, etc., follows that of FIGS. 13 and 14. FIG. 16 shows an alternative focus configuration where the system contains second focusing camera 1641, which can be a quadrant detector, PSD, or similar detector to measure the location of the reflected beam reflected from the surface. This configuration allows for focus control concurrent with data collection. The focus laser wavelength is optionally longer than the reddest dye emission filter.

Illumination Systems

A variety of illumination systems may be used in devices according to the present invention. The illumination systems can comprise lamps and/or lasers. In particular embodiments, excitation generated from a lamp or laser can be optically filtered to select a desired wavelength for illumination of a sample. The systems can contain one or more illumination lasers of different wavelengths. For example the systems herein may contain two lasers of 532 nm and 660 nm, although lasers with other wavelengths may also be used. Additionally, in various embodiments, the lasers in the systems herein are actively temperature controlled to 0.1 C., have TTL modulation for the 660 nm laser diode with rise time less than 100 ms; have integrated manual shutters for fast modulation of the 532 nm laser, have integrated beam shaping optics to ensure the optimum beam aspect ratio is maintained at the instrument interface to maximize signal to noise ratio, have integrated mode scrambler to reduce ripple on the output of the multi-mode fiber, and have minimal heat generation. The shutters and TTL modulation are used to ensure that the illumination is only on the sample surface whilst the camera is recording images. Illumination of fluorophores can cause photobleaching, and therefore exposure of substrates to the laser when not needed is generally minimized, especially before the images are recorded.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The invention claimed is:

1. A detection system for separately detecting different wavelengths of emission light emitted from a sample, the system comprising:
    a detection assembly to receive the emission light emitted from the sample, the detection assembly including a multi-band dichroic member and at least first and second detection devices, the multi-band dichroic member having a transmission/reflection characteristic with first and second transmissive regions and a reflective region along a wavelength spectrum, the reflective region extending between the first and second transmissive regions along the wavelength spectrum, the dichroic member transmitting portions of the emission light that align with the first and second transmissive regions to the first detection device, the dichroic member reflecting a portion of the emission light that aligns with the reflective region to the second detection device.

2. The system of claim 1, further comprising an excitation assembly to excite the sample, wherein the dichroic member comprises a single dichroic mirror having the first and second transmissive regions, the portions of the emissions light that are transmitted include a first portion emitted in response to a first excitation wavelength and a second portion emitted in response to a second excitation wavelength, wherein the first and second portions are transmitted by the first and second transmissive regions, respectively.

3. The detection system of claim 1, wherein the reflective region is a first reflective region and the transmission/reflection characteristic has a second reflective region, and wherein the dichroic member comprises a single dichroic mirror having an incident surface with the transmission/reflection characteristic comprising the first and second transmissive regions and the first and second reflective regions, the first transmissive region transmitting and the first reflective region reflecting respective portions of the emission light that are emitted in response to a first excitation wavelength, the second transmissive region transmitting and the second reflective region reflecting respective portions of the emission light that are emitted in response to a second excitation wavelength, wherein the respective portions of the emission light emitted in response to the first and second excitation wavelengths are transmitted or reflected at a common active area of the incident surface.

4. The system of claim 1, further comprising an excitation assembly to excite the sample, wherein the excitation assembly sequentially generates first and second excitation beams of different wavelengths during a cycle of an analysis process, the first and second excitation beams being generated repeatedly during consecutive cycles of the analysis process.

5. The detection system of claim 1, wherein the detection assembly further comprises a dual band pass filter aligned between the dichroic member and the first detection device, the dual band pass filter having first and second pass bands that are separated from each other along a wavelength spectrum.

6. The system of claim 5, wherein the first and second detection devices, the dual band pass filter, and the dichroic member constitute non-moving parts that remain stationary and fixed with respect to one another throughout an analysis process.

7. The system of claim 1, wherein the emission light includes first and second spectral patterns that are emitted in response to a first excitation event, the first detection device detecting the first spectral pattern and the second detection device detecting the second spectral pattern concurrently.

8. The system of claim 1, wherein the emission light includes first and third spectral patterns that are emitted in response to first and second excitation events, the first detection device detecting the first and third spectral patterns.

9. The system of claim 1, wherein the emission light includes at least four different spectral patterns, and wherein, in response to first and second excitation events, the dichroic member reflects at least two of the spectral patterns and transmits another two of the spectral patterns.

10. A method for detecting the emission light from the sample using the system of claim 1, the method comprising:
    exciting the sample with at least first and second excitation wavelengths, the sample having first, second, and third labels, each label emitting fluorescence of a different spectral pattern, the first and second labels being excited by the first excitation wavelength and the third label being excited by the second excitation wavelength, wherein the emission light includes the fluorescence emitted from the first, second, and third labels;
    transmitting the portions of the emission light that align with the transmissive regions through the dichroic member along a transmissive detection path to the first detection device;
    reflecting the portion of the emission light that aligns with the reflective region from the dichroic member along a reflective detection path to the second detection device; and
    detecting the emission light at the first and second detection devices, such that the fluorescence of the first and second labels are detected concurrently on different ones of the first and second detection devices, and the fluorescence of the first and third labels are detected on a common one of the first and second detection devices.

11. The method of claim 10, wherein the dichroic member comprises a single dichroic mirror having an incident surface with the transmission/reflection characteristic comprising the first and second transmissive regions, the first transmissive region transmitting the fluorescence emitted in response to the first excitation wavelength, the second transmissive region transmitting the fluorescence emitted in response to the second excitation wavelength.

12. The method of claim 10, wherein the reflective region is a first reflective region and the transmission/reflection characteristic has a second reflective region, and wherein the dichroic member comprises a single dichroic mirror having an incident surface with the transmission/reflection characteristic comprising the first and second transmissive regions and the first and second reflective regions, the first transmissive region transmitting and the first reflective region reflecting different portions of the fluorescence emitted in response to the first excitation wavelength, the second transmissive region transmitting and the second reflective region reflecting different portions of the fluorescence emitted in response to the second excitation wavelength.

13. The method of claim 10, wherein the exciting operation sequentially generates the first and second excitation wavelengths during a cycle of an analysis process, the first and second excitation wavelengths each causing the sample to emit fluorescence with at least two spectral patterns of interest that are directed by the dichroic member along the transmissive and reflective detection paths.

14. The method of claim 10, further comprising aligning at least one dual band pass filter between the dichroic member and at least one of the first and second detection devices, the dual band pass filter having at least two pass bands.

15. The method of claim 10, wherein the detecting operation detects the fluorescence based upon the transmission/reflection characteristic of the dichroic member.

16. The method of claim 10, further comprising aligning the first and second detection devices with the dichroic member such that the fluorescence transmitted through the dichroic member impinges on the first detection device and the fluorescence reflected by the dichroic member impinges on the second detection device.

17. The method of claim 10, wherein the fluorescence includes at least three different spectral patterns that are emitted in response to first and second excitation beams, the dichroic member reflecting at least one of the spectral patterns and transmitting at least two of the spectral patterns.

18. The method of claim 10, wherein the sample further comprises a fourth label, each of the first, second, third, and fourth labels emitting fluorescence having a different spectral pattern, and wherein, in response to the first and second excitation wavelengths, the dichroic member reflects at least two of the spectral patterns and transmits another two of the spectral patterns.

19. The method of claim 17, wherein the at least three different spectral patterns include first, second, and third spectral patterns have first, second, and third peaks, respectively, the first, second, and third peaks being located at separate and discrete wavelengths along the wavelength spectrum, wherein at least one of the first, second, and third spectral patterns partially overlaps another one of the spectral patterns.

20. The system of claim 1, wherein the dichroic member is configured such that the emission light that is transmitted includes first and third spectral patterns and the emission light that is reflected includes a second spectral pattern, the second spectral pattern including wavelengths between the first and third spectral patterns along the wavelength spectrum.

21. The system of claim 1, wherein the dichroic member has an incident surface with a common active area, the common active area configured to transmit the portions of the emission light that align with the first and second transmissive regions and configured to reflect the portion of the emission light that aligns with the reflective region.

22. The system of claim 1, wherein the portions of the emission light transmitted by the first and second transmissive regions are detected by the first detection device.

23. The system of claim 3, wherein the portions of the emission light reflected by the first and second reflective regions are detected by the second detection device.

24. The system of claim 1, wherein the detection assembly further comprises a dual band pass filter aligned between the dichroic member and one of the first and second detection devices.

25. The system of claim 5, wherein the dual band pass filter is a first dual band pass filter and the detection assembly further comprises a second dual band pass filter, the first dual band pass filter being aligned between the dichroic member and the first detection device, the second dual band pass filter being aligned between the dichroic member and the second detection device.

26. The system of claim 20, wherein the dichroic member has an incident surface with a common active area, the common active area configured to transmit the emission light that includes first and third spectral patterns and reflect the emission light that includes the second spectral pattern.

* * * * *